(12) United States Patent
Makower et al.

(10) Patent No.: US 9,713,483 B2
(45) Date of Patent: Jul. 25, 2017

(54) CATHETERS AND RELATED DEVICES FOR FORMING PASSAGEWAYS BETWEEN BLOOD VESSELS OR OTHER ANATOMICAL STRUCTURES

(71) Applicant: Medtronic Vascular, Inc., Santa Rosa, CA (US)

(72) Inventors: Joshua Makower, Los Altos, CA (US); J. Christopher Flaherty, Los Altos, CA (US); Timothy R. Machold, Moss Beach, CA (US); Jason B. Whitt, San Francisco, CA (US); Philip Christopher Evard, Palo Alto, CA (US); Patrick Edward Macaulay, San Jose, CA (US); John Thomas Garibotto, Newark, CA (US); Margaret W Tumas, Orinda, CA (US); Alan Robert Selfridge, Los Gatos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 45 days.

(21) Appl. No.: 14/199,901

(22) Filed: Mar. 6, 2014

(65) Prior Publication Data
US 2014/0236207 A1 Aug. 21, 2014

Related U.S. Application Data

(60) Continuation of application No. 12/634,850, filed on Dec. 10, 2009, now Pat. No. 8,753,366, which is a (Continued)

(51) Int. Cl.
*A61B 17/34* (2006.01)
*A61B 17/11* (2006.01)
(Continued)

(52) U.S. Cl.
CPC .......... *A61B 17/3439* (2013.01); *A61B 8/12* (2013.01); *A61B 17/11* (2013.01);
(Continued)

(58) Field of Classification Search
CPC ..... A61B 17/11; A61B 17/34; A61B 17/3403; A61B 17/3417; A61B 17/3421;
(Continued)

(56) References Cited

U.S. PATENT DOCUMENTS

| 3,752,162 A | 8/1973 | Newash |
| 4,602,624 A | 7/1986 | Naples et al. |

(Continued)

FOREIGN PATENT DOCUMENTS

| CA | 2384866 | 4/2001 |
| CA | 2575458 | 3/2006 |

(Continued)

OTHER PUBLICATIONS

Allen, E.V., Sympathectomy for essential hypertension, Circulation, 1952, 6:131-140.

(Continued)

*Primary Examiner* — Ryan J Severson

(57) ABSTRACT

The inventions described in this patent application include i) a torqueable introducer sheath which is useable in conjunction with a transvascular passageway forming catheter to effect precise rotational control of the catheter; ii) an anchorable guide catheter which is useable in conjunction with an intravascular imaging catheter and a transvascular passageway-forming catheter to effect precise positioning and aiming of the passageway-forming catheter; iii) a passageway forming catheter having a torqueable proximal portion to facilitate precise rotational positioning of the distal portion of the catheter; iv) a deflectable-tipped passageway forming catheter, v) various markers and other (Continued)

apparatus useable in conjunction with any of the passageway-forming catheters to facilitate precise positioning and aiming of the catheter, and vi) an apparatus which may be formed within a catheter to prevent a member, apparatus of flow of material from being inadvertently advanced through a lumen of the catheter.

8 Claims, 12 Drawing Sheets

Related U.S. Application Data division of application No. 09/912,122, filed on Jul. 24, 2001, now Pat. No. 7,648,517, which is a division of application No. 08/837,294, filed on Apr. 11, 1997, now Pat. No. 6,302,875.

(51) Int. Cl.

| | | |
|---|---|---|
| *A61M 25/10* | (2013.01) | |
| *A61B 8/12* | (2006.01) | |
| *A61B 17/12* | (2006.01) | |
| *A61B 17/3207* | (2006.01) | |
| *A61F 2/24* | (2006.01) | |
| *A61B 8/00* | (2006.01) | |
| *A61B 17/00* | (2006.01) | |
| *A61B 17/064* | (2006.01) | |
| *A61B 18/00* | (2006.01) | |
| *A61B 18/14* | (2006.01) | |
| *A61B 17/22* | (2006.01) | |
| *A61B 17/30* | (2006.01) | |
| *A61F 2/30* | (2006.01) | |
| *A61M 25/00* | (2006.01) | |
| *A61M 25/01* | (2006.01) | |
| *A61M 29/00* | (2006.01) | |
| *A61M 29/02* | (2006.01) | |
| *A61B 90/40* | (2016.01) | |
| *A61B 90/00* | (2016.01) | |

(52) U.S. Cl.
CPC .. *A61B 17/12022* (2013.01); *A61B 17/12045* (2013.01); *A61B 17/12109* (2013.01); *A61B 17/12136* (2013.01); *A61B 17/3207* (2013.01); *A61B 17/3417* (2013.01); *A61F 2/2493* (2013.01); *A61B 8/445* (2013.01); *A61B 8/4488* (2013.01); *A61B 17/00491* (2013.01); *A61B 17/0643* (2013.01); *A61B 18/00* (2013.01); *A61B 18/1477* (2013.01); *A61B 18/1492* (2013.01); *A61B 90/39* (2016.02); *A61B 90/40* (2016.02); *A61B 2017/003* (2013.01); *A61B 2017/00243* (2013.01); *A61B 2017/00247* (2013.01); *A61B 2017/00252* (2013.01); *A61B 2017/00504* (2013.01); *A61B 2017/1107* (2013.01); *A61B 2017/1139* (2013.01); *A61B 2017/12127* (2013.01); *A61B 2017/22067* (2013.01); *A61B 2017/22068* (2013.01); *A61B 2017/22069* (2013.01); *A61B 2017/22072* (2013.01); *A61B 2017/306* (2013.01); *A61B 2017/347* (2013.01); *A61B 2018/00392* (2013.01); *A61B 2018/1425* (2013.01); *A61B 2090/0811* (2016.02); *A61B 2090/378* (2016.02); *A61B 2090/3925* (2016.02); *A61B 2090/3929* (2016.02); *A61F 2002/30079* (2013.01); *A61F 2210/009* (2013.01); *A61M 25/0084* (2013.01); *A61M 25/0141* (2013.01); *A61M 25/0147* (2013.01); *A61M 25/0155* (2013.01); *A61M 29/00* (2013.01); *A61M 29/02* (2013.01); *A61M 2025/009* (2013.01); *A61M 2025/0076* (2013.01); *A61M 2025/1052* (2013.01)

(58) Field of Classification Search
CPC ............ A61B 17/3439; A61B 17/3474; A61B 17/3478; A61B 2017/00252; A61B 2017/1107; A61B 2017/22068; A61B 2017/3405; A61B 2017/3409; A61B 2017/3454; A61F 2/2493; A61M 25/0084; A61M 25/10; A61M 25/1002; A61M 2025/0089; A61M 2025/009; A61M 2025/0092; A61M 2025/0095; A61M 2025/0096; A61M 2025/1047
See application file for complete search history.

(56) References Cited

U.S. PATENT DOCUMENTS

| | | |
|---|---|---|
| 4,649,936 A | 3/1987 | Ungar et al. |
| 4,709,698 A | 12/1987 | Johnston et al. |
| 4,764,504 A | 8/1988 | Johnson et al. |
| 4,824,436 A | 4/1989 | Wolinsky |
| 4,890,623 A | 1/1990 | Cook et al. |
| 4,905,667 A | 3/1990 | Foerster et al. |
| 4,976,711 A | 12/1990 | Parins et al. |
| 5,087,244 A | 2/1992 | Wolinsky et al. |
| 5,102,402 A | 4/1992 | Dror et al. |
| 5,300,068 A | 4/1994 | Rosar et al. |
| 5,306,250 A | 4/1994 | March et al. |
| 5,326,341 A | 7/1994 | Lew et al. |
| 5,331,947 A | 7/1994 | Shturman |
| 5,344,395 A | 9/1994 | Whalen et al. |
| 5,345,940 A | 9/1994 | Seward et al. |
| 5,358,514 A | 10/1994 | Schulman et al. |
| 5,366,490 A | 11/1994 | Edwards et al. |
| 5,368,591 A | 11/1994 | Lennox et al. |
| 5,419,767 A | 5/1995 | Eggers et al. |
| 5,419,777 A | 5/1995 | Hofling |
| 5,423,744 A | 6/1995 | Gencheff et al. |
| 5,429,136 A | 7/1995 | Milo et al. |
| 5,464,395 A | 11/1995 | Faxon et al. |
| 5,484,400 A | 1/1996 | Edwards et al. |
| 5,538,504 A | 7/1996 | Linden et al. |
| 5,571,147 A | 11/1996 | Sluijter et al. |
| 5,588,960 A | 12/1996 | Edwards et al. |
| 5,588,962 A | 12/1996 | Nicholas et al. |
| 5,588,964 A | 12/1996 | Imran et al. |
| 5,590,654 A | 1/1997 | Prince |
| 5,599,345 A | 2/1997 | Edwards et al. |
| 5,626,576 A | 5/1997 | Janssen |
| 5,667,490 A | 9/1997 | Keith et al. |
| 5,672,174 A | 9/1997 | Gough et al. |
| 5,688,266 A | 11/1997 | Edwards et al. |
| 5,693,014 A | 12/1997 | Abele et al. |
| 5,700,282 A | 12/1997 | Zabara |
| 5,707,400 A | 1/1998 | Terry, Jr. et al. |
| 5,709,874 A | 1/1998 | Hanson et al. |
| 5,749,848 A | 5/1998 | Jang et al. |
| 5,772,590 A | 6/1998 | Webster, Jr. |
| 5,800,450 A | 9/1998 | Lary et al. |
| 5,817,144 A | 10/1998 | Gregory |
| 5,843,016 A | 12/1998 | Lugnani et al. |
| 5,860,974 A | 1/1999 | Abele |
| 5,865,787 A | 2/1999 | Shapland et al. |
| 5,865,801 A | 2/1999 | Houser |
| 5,876,374 A | 3/1999 | Alba et al. |
| 5,891,133 A | 4/1999 | Murphy-Chutorian |
| 5,893,885 A | 4/1999 | Webster et al. |
| 5,916,227 A | 6/1999 | Keith et al. |
| 5,924,424 A | 7/1999 | Stevens et al. |
| 5,938,670 A | 8/1999 | Keith et al. |
| 5,944,710 A | 8/1999 | Dev et al. |
| 5,954,719 A | 9/1999 | Chen et al. |
| 5,983,141 A | 11/1999 | Sluijter et al. |
| 5,989,208 A | 11/1999 | Nita |

(56) References Cited

U.S. PATENT DOCUMENTS

| | | |
|---|---|---|
| 5,997,497 A | 12/1999 | Nita et al. |
| 6,004,269 A | 12/1999 | Crowley et al. |
| 6,009,877 A | 1/2000 | Edwards |
| 6,010,480 A | 1/2000 | Abele et al. |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,117,128 A | 9/2000 | Gregory |
| 6,135,999 A | 10/2000 | Fanton et al. |
| 6,149,620 A | 11/2000 | Baker et al. |
| 6,161,048 A | 12/2000 | Sluijter et al. |
| 6,190,353 B1 | 2/2001 | Makower et al. |
| 6,211,247 B1 | 4/2001 | Goodman |
| 6,219,577 B1 | 4/2001 | Brown, III et al. |
| 6,224,592 B1 | 5/2001 | Eggers et al. |
| 6,231,516 B1 | 5/2001 | Keilman et al. |
| 6,245,045 B1 | 6/2001 | Stratienko |
| 6,246,912 B1 | 6/2001 | Sluijter et al. |
| 6,273,886 B1 | 8/2001 | Edwards et al. |
| 6,283,947 B1 | 9/2001 | Mirzaee |
| 6,283,951 B1 | 9/2001 | Flaherty et al. |
| 6,292,695 B1 | 9/2001 | Webster, Jr. et al. |
| 6,296,619 B1 | 10/2001 | Brisken et al. |
| 6,302,870 B1 | 10/2001 | Jacobsen et al. |
| 6,302,875 B1 | 10/2001 | Makower et al. |
| 6,309,379 B1 | 10/2001 | Willard et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,379,373 B1 | 4/2002 | Sawhney et al. |
| 6,389,314 B2 | 5/2002 | Feiring |
| 6,405,732 B1 | 6/2002 | Edwards et al. |
| 6,413,255 B1 | 7/2002 | Stern |
| 6,484,052 B1 | 11/2002 | Visuri et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,514,236 B1 | 2/2003 | Stratienko |
| 6,522,926 B1 | 2/2003 | Kieval et al. |
| 6,524,274 B1 | 2/2003 | Rosenthal et al. |
| 6,542,781 B1 | 4/2003 | Koblish et al. |
| 6,558,382 B2 | 5/2003 | Jahns et al. |
| 6,562,034 B2 | 5/2003 | Edwards et al. |
| 6,595,959 B1 | 7/2003 | Stratienko |
| 6,616,624 B1 | 9/2003 | Kieval |
| 6,622,731 B2 | 9/2003 | Daniel et al. |
| 6,623,452 B2 | 9/2003 | Chien et al. |
| 6,623,453 B1 | 9/2003 | Guibert et al. |
| 6,635,054 B2 | 10/2003 | Fjield et al. |
| 6,685,648 B2 | 2/2004 | Flaherty et al. |
| 6,689,086 B1 | 2/2004 | Nita et al. |
| 6,689,148 B2 | 2/2004 | Sawhney et al. |
| 6,692,738 B2 | 2/2004 | MacLaughlin et al. |
| 6,695,830 B2 | 2/2004 | Vigil et al. |
| 6,706,011 B1 | 3/2004 | Murphy-Chutorian et al. |
| 6,711,444 B2 | 3/2004 | Koblish |
| 6,714,822 B2 | 3/2004 | King et al. |
| 6,723,064 B2 | 4/2004 | Babaev |
| 6,736,835 B2 | 5/2004 | Pellegrino et al. |
| 6,752,805 B2 | 6/2004 | Maguire et al. |
| 6,767,544 B2 | 7/2004 | Brooks et al. |
| 6,788,977 B2 | 9/2004 | Fenn et al. |
| 6,830,568 B1 | 12/2004 | Kesten et al. |
| 6,845,267 B2 | 1/2005 | Harrison et al. |
| 6,849,075 B2 | 2/2005 | Bertolero et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,414 B2 | 5/2005 | Goble et al. |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 6,978,174 B2 | 12/2005 | Gelfand et al. |
| 6,991,617 B2 | 1/2006 | Hektner et al. |
| 7,066,904 B2 | 6/2006 | Rosenthal et al. |
| 7,127,284 B2 | 10/2006 | Seward |
| 7,141,041 B2 | 11/2006 | Seward |
| 7,149,574 B2 | 12/2006 | Yun et al. |
| 7,162,303 B2 | 1/2007 | Levin et al. |
| 7,197,354 B2 | 3/2007 | Sobe |
| 7,221,979 B2 | 5/2007 | Zhou et al. |
| 7,241,273 B2 | 7/2007 | Maguire et al. |
| 7,241,736 B2 | 7/2007 | Hunter et al. |
| 7,273,469 B1 | 9/2007 | Chan et al. |
| 7,297,475 B2 | 11/2007 | Koiwai et al. |
| 7,326,235 B2 | 2/2008 | Edwards |
| 7,329,236 B2 | 2/2008 | Kesten et al. |
| 7,335,192 B2 | 2/2008 | Keren et al. |
| 7,364,566 B2 | 4/2008 | Elkins et al. |
| 7,381,200 B2 | 6/2008 | Katoh et al. |
| 7,390,894 B2 | 6/2008 | Weinshilboum et al. |
| 7,407,671 B2 | 8/2008 | McBride et al. |
| 7,413,556 B2 | 8/2008 | Zhang et al. |
| 7,465,298 B2 | 12/2008 | Seward et al. |
| 7,481,803 B2 | 1/2009 | Kesten et al. |
| 7,485,104 B2 | 2/2009 | Kieval |
| 7,507,235 B2 | 3/2009 | Keogh et al. |
| 7,529,589 B2 | 5/2009 | Williams et al. |
| 7,540,870 B2 | 6/2009 | Babaev |
| 7,558,625 B2 | 7/2009 | Levin et al. |
| 7,563,247 B2 | 7/2009 | Maguire et al. |
| 7,599,730 B2 | 10/2009 | Hunter et al. |
| 7,617,005 B2 | 11/2009 | Demarais et al. |
| 7,620,451 B2 | 11/2009 | Demarais et al. |
| 7,640,046 B2 | 12/2009 | Pastore et al. |
| 7,647,115 B2 | 1/2010 | Levin et al. |
| 7,648,517 B2 | 1/2010 | Makower et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,706,882 B2 | 4/2010 | Francischelli et al. |
| 7,717,948 B2 | 5/2010 | Demarais et al. |
| 7,744,584 B2 | 6/2010 | Seward et al. |
| 7,766,892 B2 | 8/2010 | Keren et al. |
| 7,778,703 B2 | 8/2010 | Gross et al. |
| 7,837,720 B2 | 11/2010 | Mon |
| 7,905,862 B2 | 3/2011 | Sampson |
| 7,917,208 B2 | 3/2011 | Yomtov et al. |
| 1,010,406 A1 | 5/2011 | Seward |
| 1,018,291 A1 | 7/2011 | Evans et al. |
| 1,018,433 A1 | 7/2011 | Evans et al. |
| 8,016,786 B2 | 9/2011 | Seward et al. |
| 8,027,740 B2 | 9/2011 | Altman et al. |
| 8,119,183 B2 | 2/2012 | O'Donoghue et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,162,933 B2 | 4/2012 | Francischelli et al. |
| 8,175,711 B2 | 5/2012 | Demarais et al. |
| 8,257,724 B2 | 9/2012 | Cromack et al. |
| 8,257,725 B2 | 9/2012 | Cromack et al. |
| 8,263,104 B2 | 9/2012 | Ho et al. |
| 8,317,776 B2 | 11/2012 | Ferren et al. |
| 8,388,680 B2 | 3/2013 | Starksen et al. |
| 8,396,548 B2 | 3/2013 | Perry et al. |
| 8,399,443 B2 | 3/2013 | Seward |
| 8,403,881 B2 | 3/2013 | Ferren et al. |
| 8,465,752 B2 | 6/2013 | Seward |
| 8,562,573 B1 | 10/2013 | Fischell |
| 8,663,190 B2 | 3/2014 | Fischell et al. |
| 8,708,995 B2 | 4/2014 | Seward et al. |
| 8,721,590 B2 | 5/2014 | Seward et al. |
| 8,740,849 B1 | 6/2014 | Fischell et al. |
| 8,753,366 B2 | 6/2014 | Makower et al. |
| 8,975,233 B2 | 3/2015 | Stein et al. |

(56) References Cited

U.S. PATENT DOCUMENTS

| | | |
|---|---|---|
| 9,055,956 B2 | 6/2015 | McRae et al. |
| 2001/0039419 A1 | 11/2001 | Francischelli et al. |
| 2002/0077592 A1 | 6/2002 | Barry |
| 2002/0082552 A1 | 6/2002 | Ding et al. |
| 2002/0103445 A1 | 8/2002 | Rahdert et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0069619 A1 | 4/2003 | Fenn et al. |
| 2003/0074039 A1 | 4/2003 | Puskas |
| 2003/0082225 A1 | 5/2003 | Mason |
| 2003/0114791 A1 | 6/2003 | Rosenthal et al. |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0064093 A1 | 4/2004 | Hektner et al. |
| 2004/0186468 A1 | 9/2004 | Edwards |
| 2004/0215186 A1 | 10/2004 | Cornelius et al. |
| 2004/0253304 A1 | 12/2004 | Gross et al. |
| 2005/0080409 A1 | 4/2005 | Young et al. |
| 2005/0149173 A1 | 7/2005 | Hunter et al. |
| 2005/0149175 A1 | 7/2005 | Hunter et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165467 A1 | 7/2005 | Hunter et al. |
| 2005/0175661 A1 | 8/2005 | Hunter et al. |
| 2005/0175662 A1 | 8/2005 | Hunter et al. |
| 2005/0177103 A1 | 8/2005 | Hunter et al. |
| 2005/0181004 A1 | 8/2005 | Hunter et al. |
| 2005/0182479 A1 | 8/2005 | Bonsignore et al. |
| 2005/0186242 A1 | 8/2005 | Hunter et al. |
| 2005/0186243 A1 | 8/2005 | Hunter et al. |
| 2005/0187579 A1 | 8/2005 | Danek et al. |
| 2005/0192638 A1 | 9/2005 | Gelfand et al. |
| 2005/0228286 A1 | 10/2005 | Messerly et al. |
| 2005/0228460 A1 | 10/2005 | Levin et al. |
| 2005/0267556 A1 | 12/2005 | Shuros et al. |
| 2005/0283195 A1 | 12/2005 | Pastore et al. |
| 2006/0018949 A1 | 1/2006 | Ammon et al. |
| 2006/0025821 A1 | 2/2006 | Gelfand et al. |
| 2006/0041277 A1 | 2/2006 | Deem et al. |
| 2006/0085054 A1 | 4/2006 | Zikorus et al. |
| 2006/0095029 A1 | 5/2006 | Young et al. |
| 2006/0111672 A1 | 5/2006 | Seward |
| 2006/0189941 A1 | 8/2006 | Seward et al. |
| 2006/0206150 A1 | 9/2006 | Demarais et al. |
| 2006/0212076 A1 | 9/2006 | Demarais et al. |
| 2006/0240070 A1 | 10/2006 | Cromack et al. |
| 2006/0263393 A1 | 11/2006 | Demopulos et al. |
| 2006/0271111 A1 | 11/2006 | Demarais et al. |
| 2006/0280858 A1 | 12/2006 | Kokish |
| 2007/0066959 A1 | 3/2007 | Seward |
| 2007/0078620 A1 | 4/2007 | Seward et al. |
| 2007/0100318 A1 | 5/2007 | Seward et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0118107 A1 | 5/2007 | Francischelli et al. |
| 2007/0129720 A1 | 6/2007 | Demarais et al. |
| 2007/0207186 A1 | 9/2007 | Scanlon et al. |
| 2007/0208134 A1 | 9/2007 | Hunter et al. |
| 2007/0219576 A1 | 9/2007 | Cangialosi |
| 2007/0248639 A1 | 10/2007 | Demopulos et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0299043 A1 | 12/2007 | Hunter et al. |
| 2008/0004596 A1 | 1/2008 | Yun et al. |
| 2008/0039746 A1 | 2/2008 | Hissong et al. |
| 2008/0045890 A1 | 2/2008 | Seward et al. |
| 2008/0086072 A1 | 4/2008 | Bonutti et al. |
| 2008/0208162 A1 | 8/2008 | Joshi |
| 2008/0213331 A1 | 9/2008 | Gelfand et al. |
| 2008/0245371 A1 | 10/2008 | Gruber |
| 2008/0317818 A1 | 12/2008 | Griffith et al. |
| 2008/0319513 A1 | 12/2008 | Pu et al. |
| 2009/0036948 A1 | 2/2009 | Levin et al. |
| 2009/0074828 A1 | 3/2009 | Alexis et al. |
| 2009/0105631 A1 | 4/2009 | Kieval |
| 2009/0142306 A1 | 6/2009 | Seward et al. |
| 2009/0156988 A1 | 6/2009 | Ferren et al. |
| 2009/0157057 A1 | 6/2009 | Ferren et al. |
| 2009/0216317 A1 | 8/2009 | Cromack et al. |
| 2009/0221955 A1 | 9/2009 | Babaev |
| 2010/0069837 A1 | 3/2010 | Rassat et al. |
| 2010/0087782 A1 | 4/2010 | Ghaffari et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0217162 A1 | 8/2010 | Hissong et al. |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249702 A1 | 9/2010 | Magana et al. |
| 2010/0324472 A1 | 12/2010 | Wulfman |
| 2011/0137155 A1 | 6/2011 | Weber et al. |
| 2011/0257622 A1 | 10/2011 | Salahieh et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |
| 2012/0259269 A1 | 10/2012 | Meyer |
| 2012/0271277 A1 | 10/2012 | Fischell et al. |
| 2012/0271301 A1 | 10/2012 | Fischell et al. |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0096604 A1 | 4/2013 | Hanson et al. |
| 2013/0172815 A1 | 7/2013 | Perry et al. |
| 2013/0204131 A1 | 8/2013 | Seward |
| 2013/0252932 A1 | 9/2013 | Seward |
| 2013/0274673 A1 | 10/2013 | Fischell et al. |
| 2013/0274674 A1 | 10/2013 | Fischell et al. |
| 2013/0287698 A1 | 10/2013 | Seward |
| 2013/0296853 A1 | 11/2013 | Sugimoto et al. |
| 2014/0012231 A1 | 1/2014 | Fischell |
| 2014/0046298 A1 | 2/2014 | Fischell et al. |
| 2014/0107478 A1 | 4/2014 | Seward et al. |
| 2014/0121641 A1 | 5/2014 | Fischell et al. |
| 2014/0121644 A1 | 5/2014 | Fischell et al. |
| 2014/0135661 A1 | 5/2014 | Garrison et al. |
| 2014/0236103 A1 | 8/2014 | Fischell et al. |
| 2014/0271717 A1 | 9/2014 | Goshayeshgar et al. |
| 2014/0276621 A1 | 9/2014 | Braga |
| 2014/0296279 A1 | 10/2014 | Seward et al. |
| 2014/0303569 A1 | 10/2014 | Seward et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |

FOREIGN PATENT DOCUMENTS

| | | |
|---|---|---|
| EP | 0233100 | 8/1987 |
| EP | 0497041 | 1/1997 |
| EP | 0774991 | 5/1997 |
| EP | 1782852 | 5/2007 |
| EP | 2352542 | 8/2011 |
| EP | 2429641 | 3/2012 |
| EP | 2528649 | 12/2012 |
| EP | 2656807 | 10/2013 |
| EP | 2675458 | 12/2013 |

(56) References Cited

FOREIGN PATENT DOCUMENTS

| | | |
|---|---|---|
| EP | 2694150 | 2/2014 |
| EP | 2747688 | 7/2014 |
| JP | 49009882 | 1/1974 |
| JP | 62181225 | 8/1987 |
| JP | 3041967 | 10/1997 |
| JP | 2003510126 | 3/2003 |
| JP | 2004016333 | 1/2004 |
| WO | WO-93/15664 | 8/1993 |
| WO | WO-9407446 | 4/1994 |
| WO | WO-9525472 | 9/1995 |
| WO | WO-9531142 | 11/1995 |
| WO | WO-9703604 | 2/1997 |
| WO | WO-9736548 | 10/1997 |
| WO | WO-9742990 | 11/1997 |
| WO | WO-9900060 | 1/1999 |
| WO | WO-0122897 | 4/2001 |
| WO | WO-0170114 | 9/2001 |
| WO | WO-02058549 | 8/2002 |
| WO | WO-03022167 | 9/2002 |
| WO | WO-03024311 | 3/2003 |
| WO | WO-03082080 | 10/2003 |
| WO | WO-2004/011055 | 2/2004 |
| WO | WO-2004/028583 | 4/2004 |
| WO | WO-2004049976 | 6/2004 |
| WO | WO-2005007000 | 1/2005 |
| WO | WO-2005030072 | 4/2005 |
| WO | WO-2005041748 | 5/2005 |
| WO | WO-2005110528 | 11/2005 |
| WO | WO-2006022790 | 3/2006 |
| WO | WO-2006041881 | 4/2006 |
| WO | WO-2007008954 | 1/2007 |
| WO | WO-2007078997 | 7/2007 |
| WO | WO-2008049084 | 4/2008 |
| WO | WO-2009088678 | 7/2009 |
| WO | WO-2010042653 | 4/2010 |
| WO | WO-2011094367 | 8/2011 |
| WO | WO-2011133724 | 10/2011 |
| WO | WO-2012161875 | 11/2012 |
| WO | WO-2013028781 | 2/2013 |
| WO | WO-2013059735 | 4/2013 |
| WO | WO-2013063331 | 5/2013 |
| WO | WO-2013112844 | 8/2013 |
| WO | WO-2013169741 | 11/2013 |
| WO | WO-2013188689 | 12/2013 |
| WO | WO-2014031167 | 2/2014 |
| WO | WO-2014070820 | 5/2014 |
| WO | WO-2014070999 | 5/2014 |
| WO | WO-2014078301 | 5/2014 |
| WO | WO-2014189887 | 11/2014 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-in-

(56) References Cited

OTHER PUBLICATIONS novation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gelfand, M., et al., "Treatment of renal failure and hypertension." Provisional U.S. Appl. No. 60/442,970, filed Jan. 29, 2003, 23 pages.
Gertner, Jon, "Meet the Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Intery Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.

(56) References Cited

OTHER PUBLICATIONS

Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN/%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding A Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.

(56) References Cited

OTHER PUBLICATIONS

Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Gonschior, P., Comparison of Local Intravascular Drug-Delivery Catheter Systems, Am. Heart J., Dec. 1995, 130:6, 1174-81.
Pieper et al., "Design and Implementation of a New Computerized System for Intraoperative Cardiac Mapping." Journal of Applied Physiology, 1991, vol. 71, No. 4, pp. 1529-1539.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
U.S. Appl. No. 60/852,787, filed Oct. 18, 2006, 112 pages.
Beale et al., "Minimally Invasive Treatment for Varicose Veins: a Review of Endovenous Laser Treatment and Radiofrequency Ablation". Lower Extremity Wounds 3(4), 2004, 10 pages.
Stella, A., et al., "Effects of reversable renal denervation on haemodynamic and excretory functions on the ipsilateral and contralateral kidney in the cat." Hypertension, 4: 181-188 (1986).

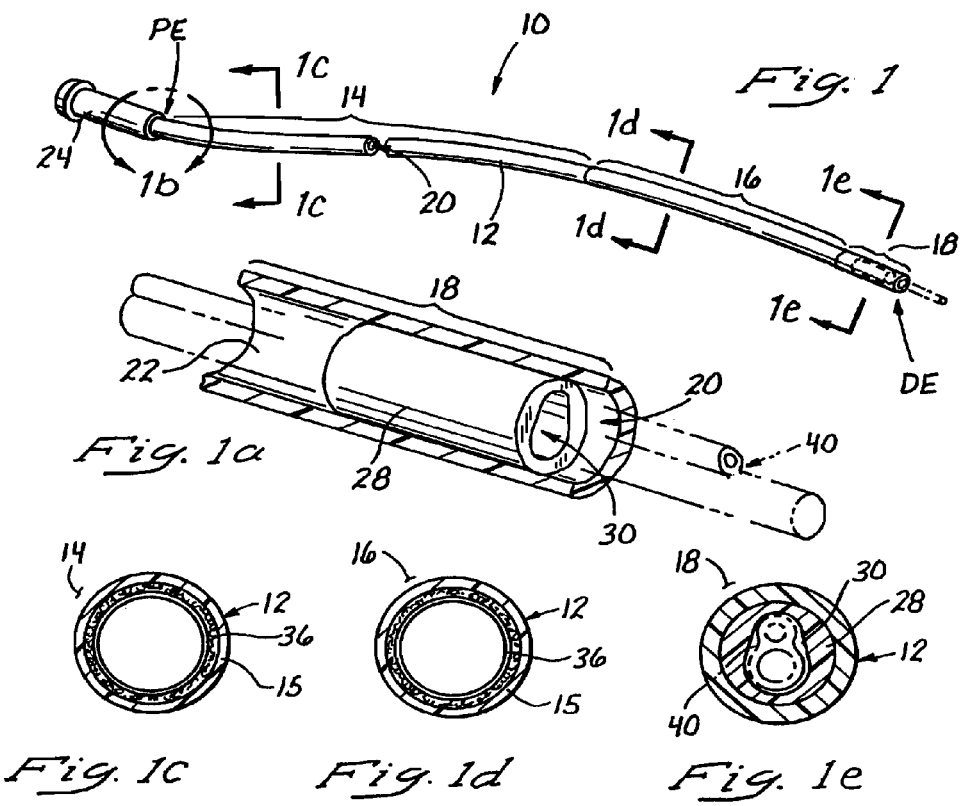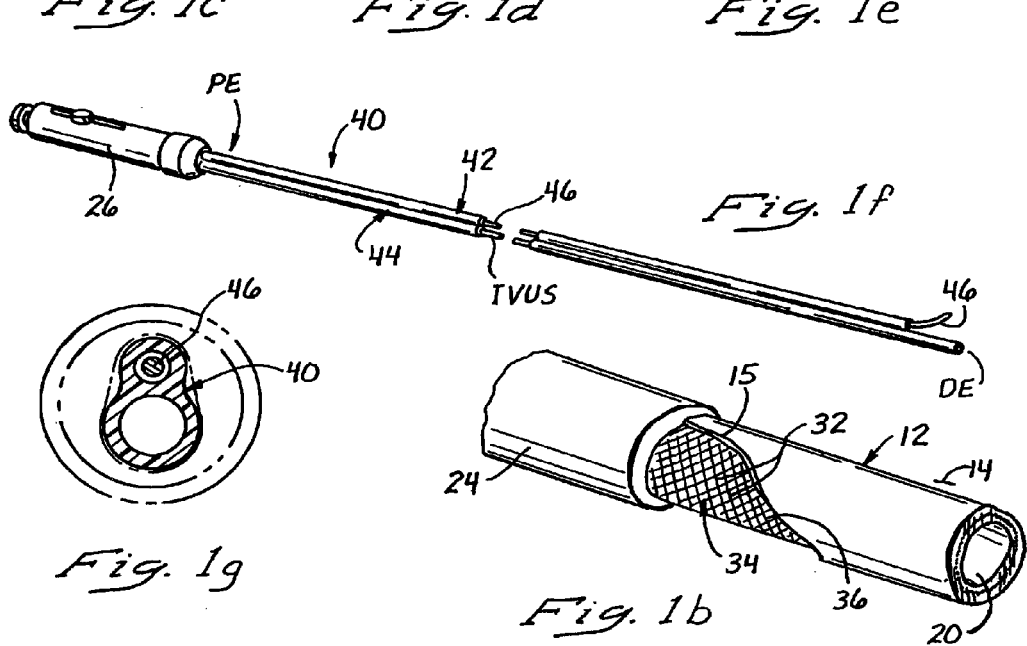

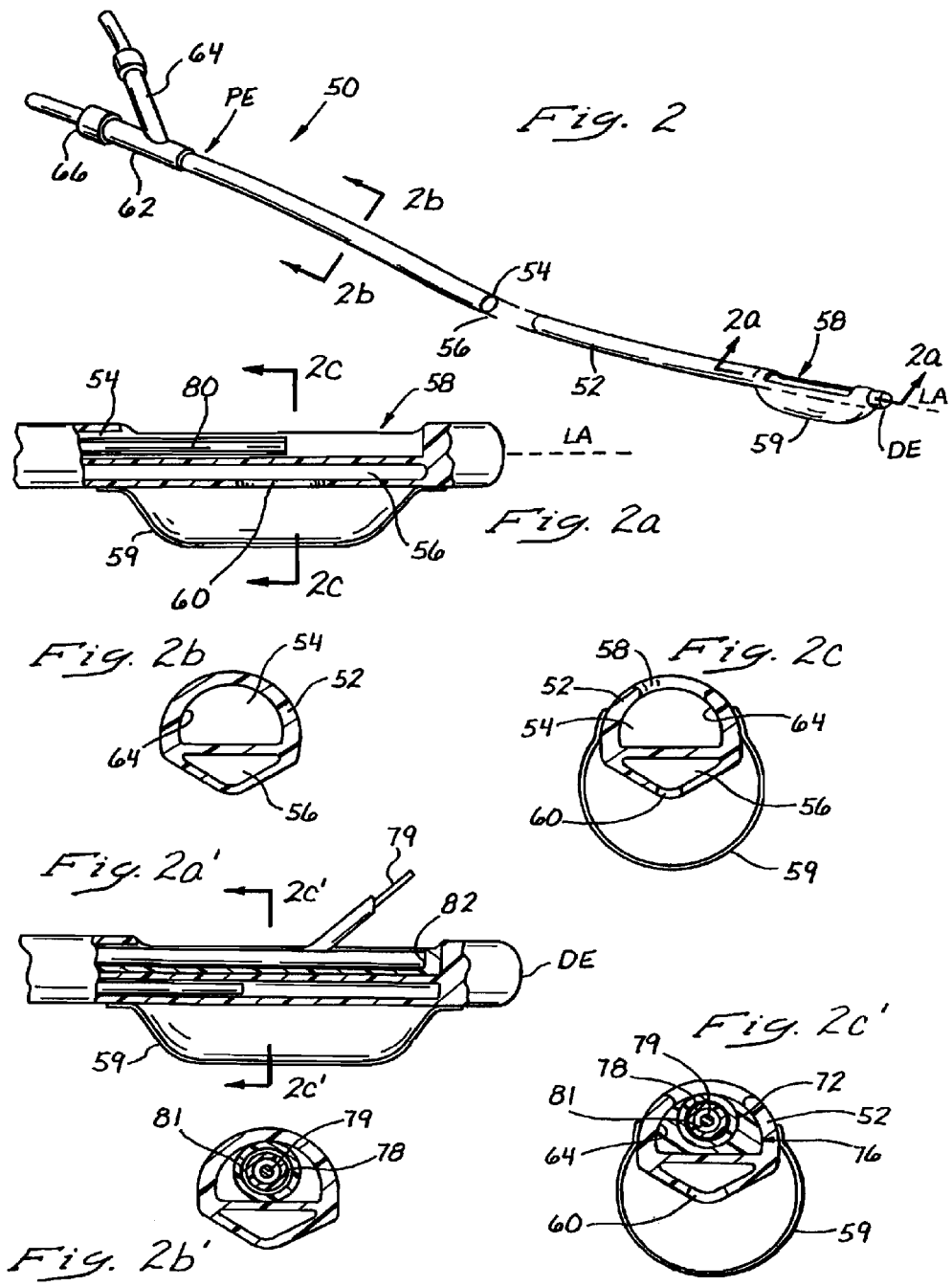

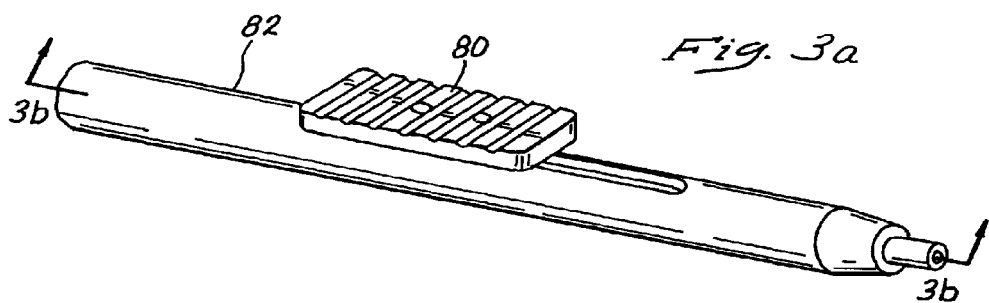
Fig. 3a
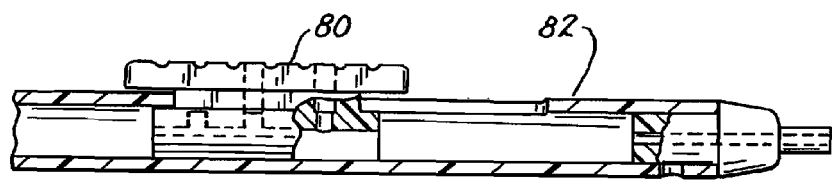
Fig. 3b
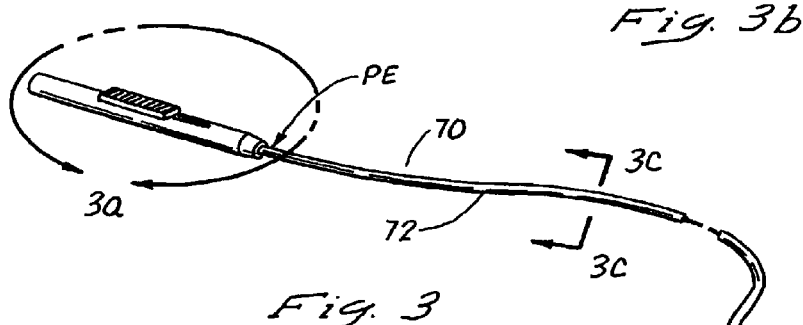
Fig. 3
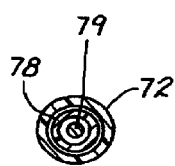
Fig. 3c
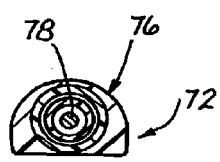
Fig. 3d
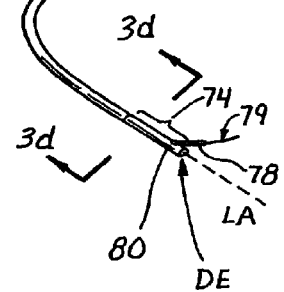

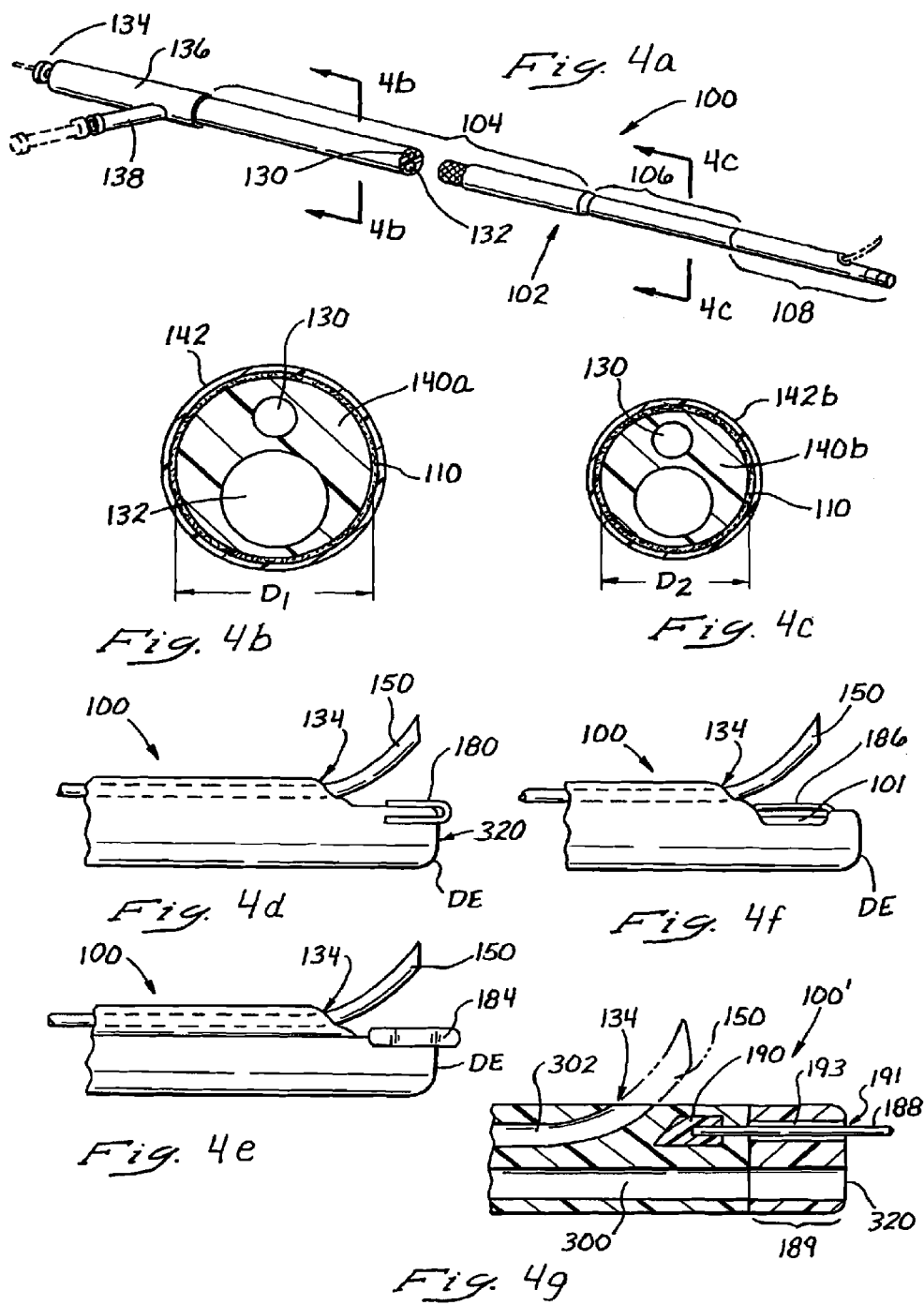

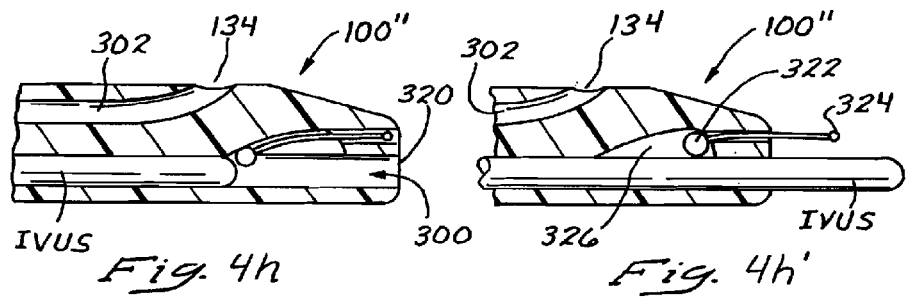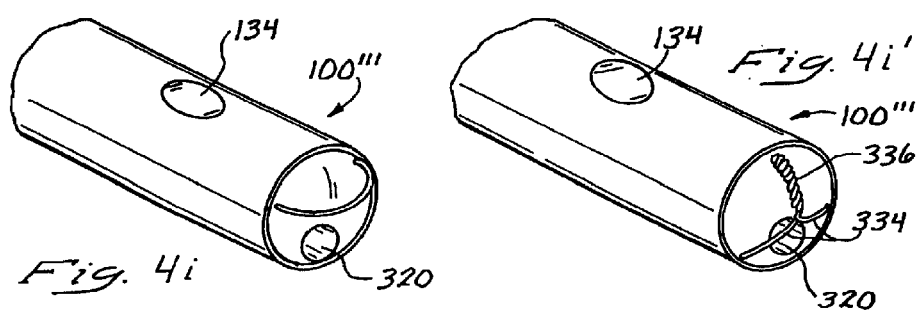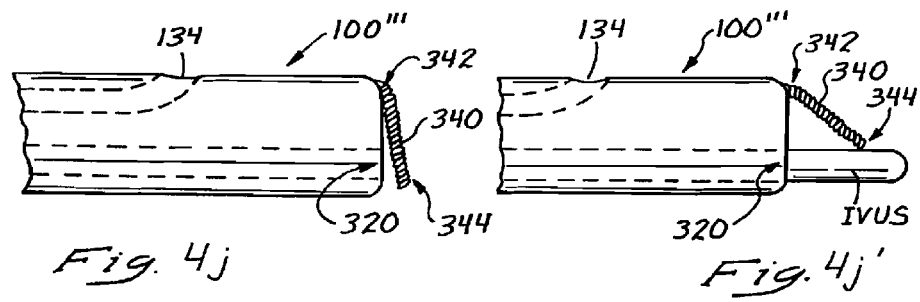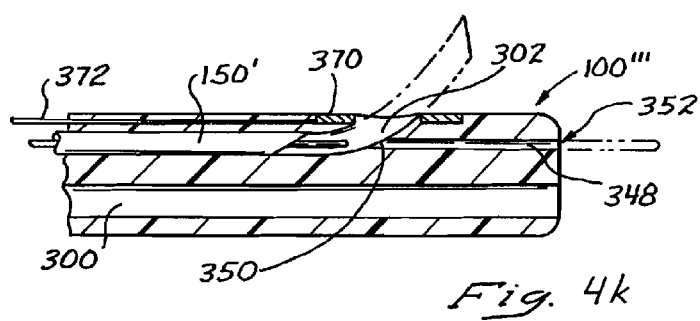

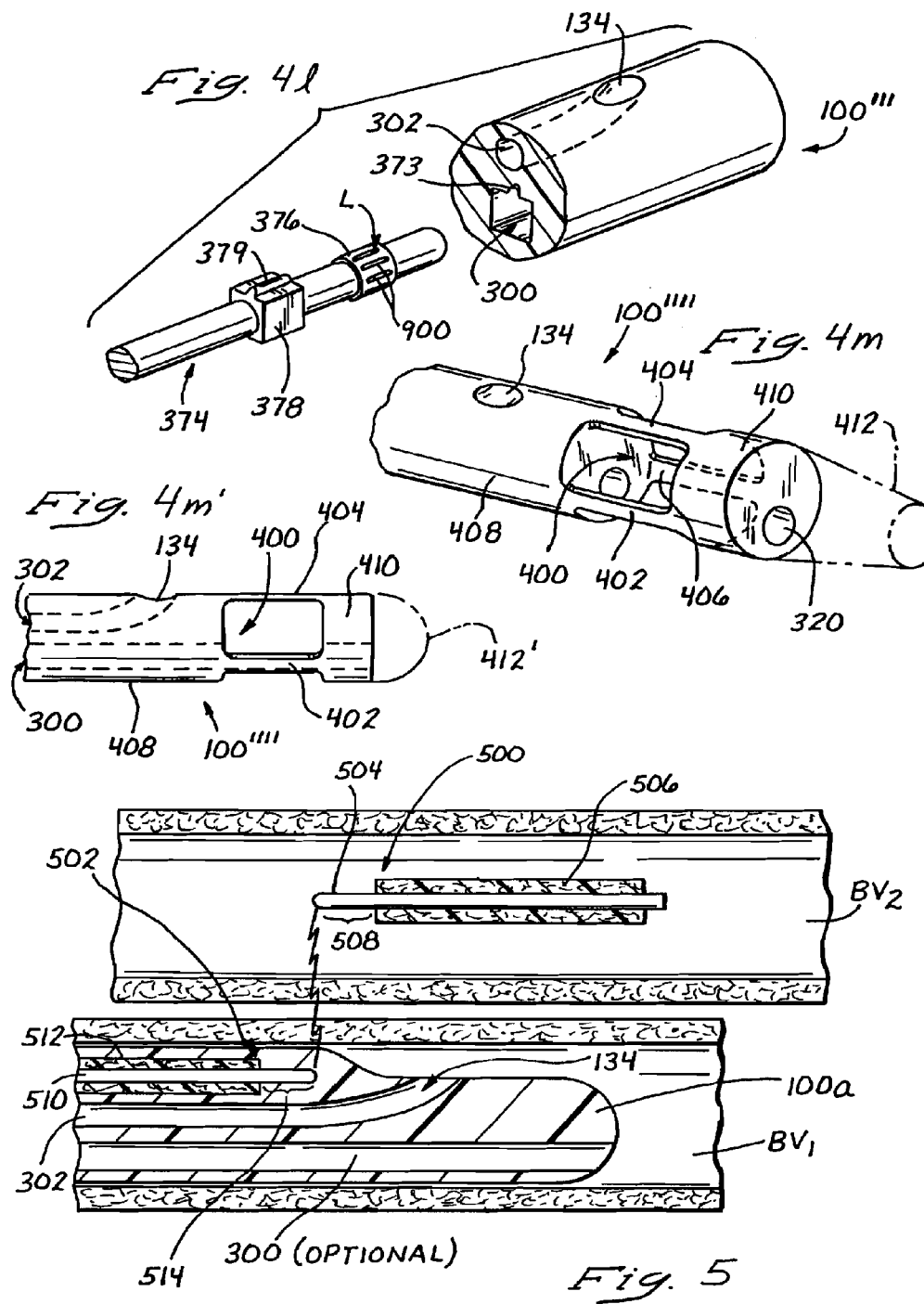

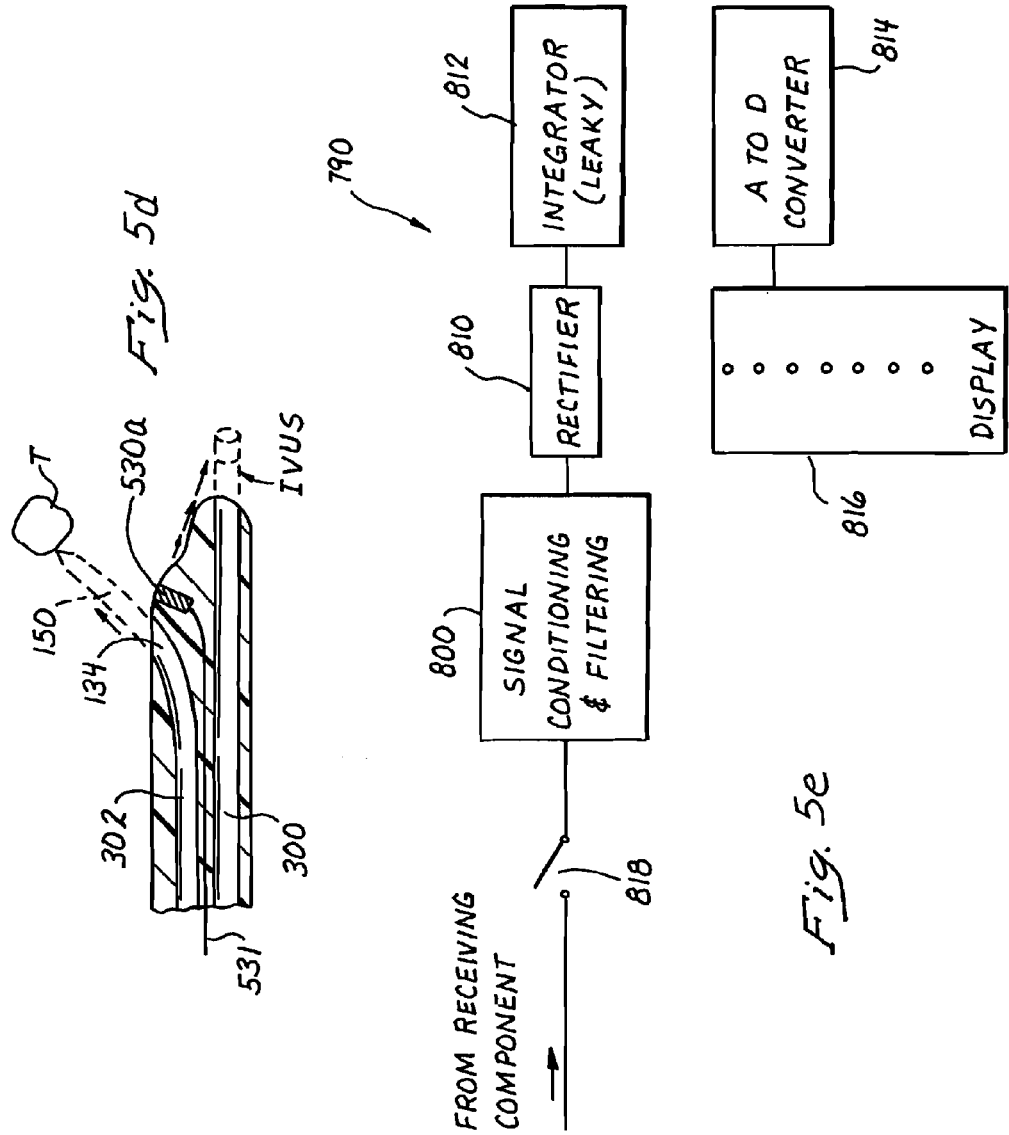

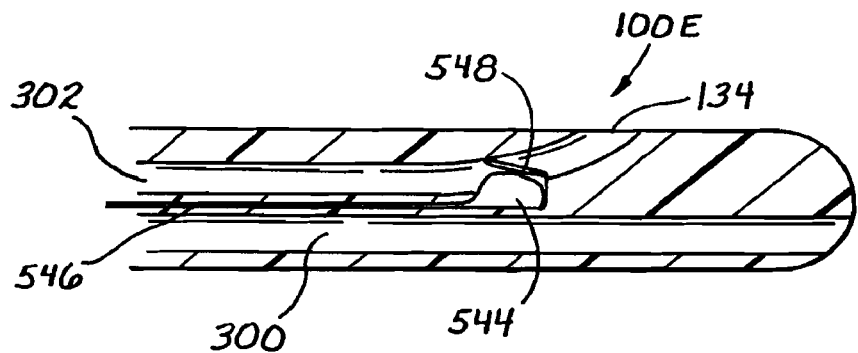
Fig. 8
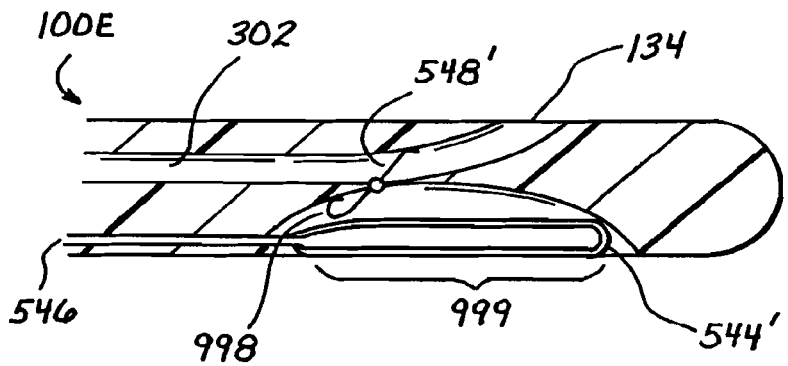
Fig. 8'
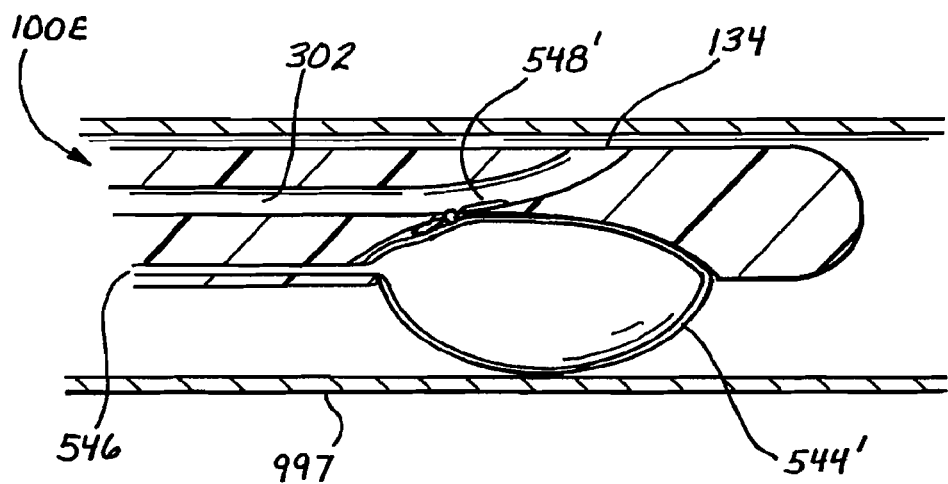
Fig. 8"

CATHETERS AND RELATED DEVICES FOR FORMING PASSAGEWAYS BETWEEN BLOOD VESSELS OR OTHER ANATOMICAL STRUCTURES

RELATED APPLICATION

This patent application is a continuation of U.S. patent application Ser. No. 12/634,850 filed Dec. 9, 2009 and issued as U.S. Pat. No. 7,648,517, which is a division of Ser. No. 09/912,122 filed Jul. 24, 2001 and issued as U.S. Pat. No. 7,648,517, which is a division of Ser. No. 08/837,294 filed Apr. 11, 1997 and issued as U.S. Pat. No. 6,302,875, the entire disclosures of which are expressly incorporated herein by reference.

FIELD OF THE INVENTION

The present invention relates generally to medical devices and methods, and more particularly to catheters, catheter positioning/aiming systems, and related methods for forming interstitial passageways (e.g., interstitial tunnels) between two or more adjacently situated blood vessels or other anatomical structures.

BACKGROUND OF THE INVENTION

Applicant has invented novel methods for bypassing obstructions in arteries and for performing other transvascular medical procedures, wherein a catheter device is inserted transluminally into the blood vessel or other luminal anatomical structure and a tissue-penetrating element (e.g., a puncturing member or a flow of energy) is passed out of the catheter, through the wall of the blood vessel or other anatomical structure in which the catheter is positioned, and into a second blood vessel or other target anatomical structure. In this manner one or more interstitial passageways is/are formed from the blood vessel or other luminal structure in which the catheter is positioned, to a second blood vessel or other target tissue. These transvascular procedures, and certain passageway forming catheters which are useable to perform these procedures, have previously been described in U.S. patent application Ser. No. 08/730,327 entitled METHODS AND APPARATUS FOR BYPASSING ARTERIAL OBSTRUCTIONS AND/OR PERFORMING OTHER TRANSVASCULAR PROCEDURES, filed on Oct. 11, 1996 and Ser. No. 08/730,496 entitled, A DEVICE, SYSTEM AND METHOD FOR INTERSTITIAL TRANSVASCULAR INTERVENTION, filed Oct. 11, 1996.

In performing the above-summarized transvascular procedures, it is important that the passageway-forming catheter be properly positioned and oriented within the body in the order to ensure that the tissue-penetrating element will form the desired interstitial passageway, at the desired location. If the catheter is improperly positioned or improperly oriented, the resultant passageway(s) may fail to perform their intended function (e.g., to channel blood from one location to another) or the tissue penetrating element of the catheter may perforate or traumatize tissue(s) other than those intended to be canalized.

In many of the passageway-forming catheters devised by applicant, it is necessary to precisely control the rotational orientation of the catheter in order to accomplish the desired aiming of the tissue-penetrating element. However, when the passageway-forming catheter is formed of relatively small diameter, thin-walled polymeric material capable of navigating small, tortuous blood vessels, the catheter shaft may lack sufficient structural integrity to efficiently transfer torque from the proximal end of the catheter to the distal end thereof. Such diminished torque transfer of the catheter shaft can prevent or interfere with the precise rotational orientation and positioning of the distal portion of the catheter prior to formation of the extravascular passageway.

Additionally, to facilitate the use of any on-board imaging system (e.g., an intravascular ultrasound system inserted or built into the passageway-forming catheter) or any separate intracorporeal or extracorporeal imaging services intended to assist in the precise aiming of the tissue-penetrating element, it is desirable for the tissue-penetrating catheter to be provided with appropriate markers or other indicia to enable the operator to utilize to discern the present rotational orientation and position of the catheter and the projected path of the tissue-penetrating element.

Thus, there remains a need in the art for further development and modification of applicant's previously described passageway-forming catheter devices so as to provide for i) improved torque transfer to the distal portion of the catheter and ii) precise rotational orientation and aiming of the catheter prior to deployment of the tissue penetrating element.

SUMMARY OF THE INVENTION

The inventions described in this patent application include i) a torqueable introducer sheath which is useable in conjunction with a transvascular passageway forming catheter to effect precise rotational control of the catheter; ii) an anchorable guide catheter which is useable in conjunction with an intravascular imaging catheter and a transvascular passageway-forming catheter to effect precise positioning and aiming of the passageway-forming catheter; iii) a passageway forming catheter having a torqueable proximal portion to facilitate precise rotational positioning of the distal portion of the catheter; iv) a deflectable-tipped passageway forming catheter, v) various markers and other apparatus useable in conjunction with any of the passageway-forming catheters to facilitate precise positioning and aiming of the catheter, and vi) an apparatus which may be formed within a catheter to prevent a member, apparatus of flow of material from being inadvertently advanced through a lumen of the catheter.

Additional details and objects of each of the above-summarized inventions will become apparent to those skilled in the art upon reading and understanding of the following detailed descriptions of preferred embodiments and the accompanying drawings.

BRIEF DESCRIPTION OF THE DRAWINGS

FIG. 1 is a perspective view of a torqueable sheath through which a passageway-forming catheter of the present invention may be inserted, and which may be used to facilitate subsequent rotational positioning of the distal portion of the passageway-forming catheter.

FIG. 1a is a cut-away perspective view of the distal end of the torqueable sheath of FIG. 1, and shown in phantom lines the preferred operative positioning of a passageway-forming catheter within such torqueable sheath.

FIG. 1b is a partial cut-away perspective view of portion 1b of FIG. 1, showing the braided wire layer formed within the proximal portion of the torqueable sheath.

FIG. 1c is a cross-sectional view through line 1c-1c of FIG. 1.

FIG. 1*d* is a cross-sectional view through line 1*d*-1*d* of FIG. 1.

FIG. 1*e* is a cross-sectional view through line 1*e*-1*e* of FIG. 1.

FIG. 1*f* is a perspective view of a typical passageway-forming catheter of Applicant's invention, as previously described in U.S. patent application Ser. No. 08/730,327, entitled METHODS AND APPARATUS FOR BYPASSING ARTERIAL OBSTRUCTIONS AND/OR PERFORMING OTHER TRANSVASCULAR PROCEDURES filed on Oct. 11, 1996.

FIG. 1*g* is a cross-sectional view through line 1*g*-1*g* of FIG. 1*f*, and additional showing in phantom lines the preferred operative positioning of a torqueable sheath of the present invention relative to that portion of the passageway-forming catheter.

FIG. 2 is a perspective view of a guide catheter of the present invention having an anchoring balloon formed on the distal end thereof.

FIG. 2*a* is a partial longitudinal sectional view through line 2*a*-2*a* of the guide catheter of FIG. 2, showing an intravascular ultrasound device operatively inserted into the guide catheter.

FIG. 2*b* is a cross-sectional view through line 2*b*-2*b* of the guide catheter FIG. 2 having an intravascular ultrasound catheter operatively inserted therethrough.

FIG. 2*c* is a cross-sectional view through line 2*c*-2*c* of FIG. 2*a*.

FIG. 2*a*' is a partial longitudinal sectional view through line 2*a*-2*a* of the guide catheter of FIG. 2, showing a passageway-forming catheter of the present invention operatively inserted into the guide catheter.

FIG. 2*b*' is a cross sectional view through line 2*b*-2*b* of the guide catheter of FIG. 2 having a passageway-forming catheter of the present invention operatively inserted therethrough.

FIG. 2*c*' is a cross-sectional view through line 2*c*'-2*c*' of FIG. 2*a*'.

FIG. 3 is a perspective view of the passageway forming catheter of the present invention which is useable in conjunction with the guide catheter shown in FIGS. 22*c*'.

FIG. 3*a* is a perspective view of portion 3*a* of FIG. 3.

FIG. 3*b* is a longitudinal sectional view through line 3*b*-3*b* of FIG. 3*a*.

FIG. 3*c* is a cross-sectional view through line 3*c*-3*c* of FIG. 3.

FIG. 3*d* is a cross-sectional view through line 3*d*-3*d* of FIG. 3.

FIG. 4*a* is a perspective view of a torqueable passageway-forming catheter device of the present invention.

FIG. 4*b* is a cross-sectional view through line 4*b*-4*b* of FIG. 4*a*.

FIG. 4*c* is a cross-sectional view through line 4*c*-4*c* of FIG. 4*a*.

FIG. 4*d* is a perspective view of the distal portion of a passageway-forming catheter of the present invention incorporating a first marker thereon.

FIG. 4*e* is a perspective view of the distal portion of a passageway forming catheter of the present invention incorporating a second marker thereon.

FIG. 4*f* is a perspective view of the distal portion of a passageway forming catheter of the present invention incorporating a third marker thereon.

FIG. 4*g* is a longitudinal sectional view of the distal portion of a passageway-forming catheter having a fourth marker of the present invention formed thereon.

FIG. 4*h* is a longitudinal section view of the distal portion of a passageway forming catheter having a fifth marker formed thereon.

FIG. 4*h*' is a longitudinal sectional view of the passageway forming catheter of FIG. 4*h* wherein the marker has been advanced to its operative position by insertion of an IVUS catheter through one lumen of the passageway-forming catheter.

FIG. 4*i* is a perspective view of the distal portion of a passageway forming catheter having a sixth marker formed thereon.

FIG. 4*i*' is a perspective view of the distal portion of a passageway forming catheter having a variation of the sixth marker of FIG. 4*i* formed thereon.

FIG. 4*j* is an elevational view of the distal portion of a passageway forming catheter having a seventh marker formed thereon.

FIG. 4*j*' is an elevational view of the distal portion of the passageway catheter of FIG. 4*j* wherein the seventh marker has been advanced to an operative position by insertion of an IVUS catheter through one lumen of the passageway forming catheter.

FIG. 4*k* is a longitudinal sectional view of the distal portion of a passageway forming catheter wherein i) a reduced-diameter guidewire lumen has been formed to permit a guidewire to be temporarily advanced into such guidewire lumen to act as a marker to facilitate precise rotational positioning of the catheter, and ii) an ultrasound chip has been mounted on the catheter adjacent the outlet opening for the tissue penetrating element so as to cause ultrasonic vibration and enhanced imageability of the tissue penetrating element when it is deployed out of the opening.

FIG. 4*l*' is a schematic diagram of one type of system which may be utilized to electronically mark or differentiate the image received from a single crystal on the phased array imaging catheter of FIG. 4*l*.

FIG. 4*m* is a perspective view of the distal portion of a passageway forming catheter having an eighth marker formed thereon.

FIG. 4*m*' is an elevational view of the distal portion of a passageway forming catheter having a variant of the eighth marker of FIG. 4*m* formed thereon.

FIG. 5 is a longitudinal sectional view of an adjacent artery and vein, showing an energy-emitting/receiving guidance and positioning system of the present invention which is useable to effect precise positioning and rotational orientation of the passageway-forming catheter.

FIG. 5d is a partial longitudinal sectional view of another passageway forming catheter of the present invention (having an alternative aiming/positioning system wherein an active (e.g., emitting) component is mounted in specific relation to the outlet port for the tissue-penetrating element, and is adapted to emit a signal to an imaging component (e.g., IVUS catheter) to accentuate the location of the outlet port and facilitate aiming of the catheter by use of the imaging device.

FIG. 5e is a schematic diagram of one type of system which may be utilized to peak a signal received from the passive (e.g., receiving) component of an aiming/positioning system of FIGS. 5-5c hereabove.

FIG. 8 is a longitudinal sectional view of another passageway-forming catheter which incorporates apparatus for preventing deployment of the tissue-penetrating element.

FIG. 8' is a longitudinal sectional view of another passageway-forming catheter which incorporates apparatus for preventing deployment of the tissue-penetrating element and for stabilizing the catheter within a luminal anatomical structure, wherein such apparatus is in an initial configuration whereby the lumen is blocked and the catheter is unstabilized.

FIG. 8" is a longitudinal sectional view of another passageway-forming catheter which incorporates apparatus for preventing deployment of the tissue-penetrating element and for stabilizing the catheter within a luminal anatomical structure, wherein such apparatus is in an operative configuration wherein the lumen is open and the catheter is stabilized.

DETAILED DESCRIPTIONS PREFERRED EMBODIMENTS

Figure 4L:
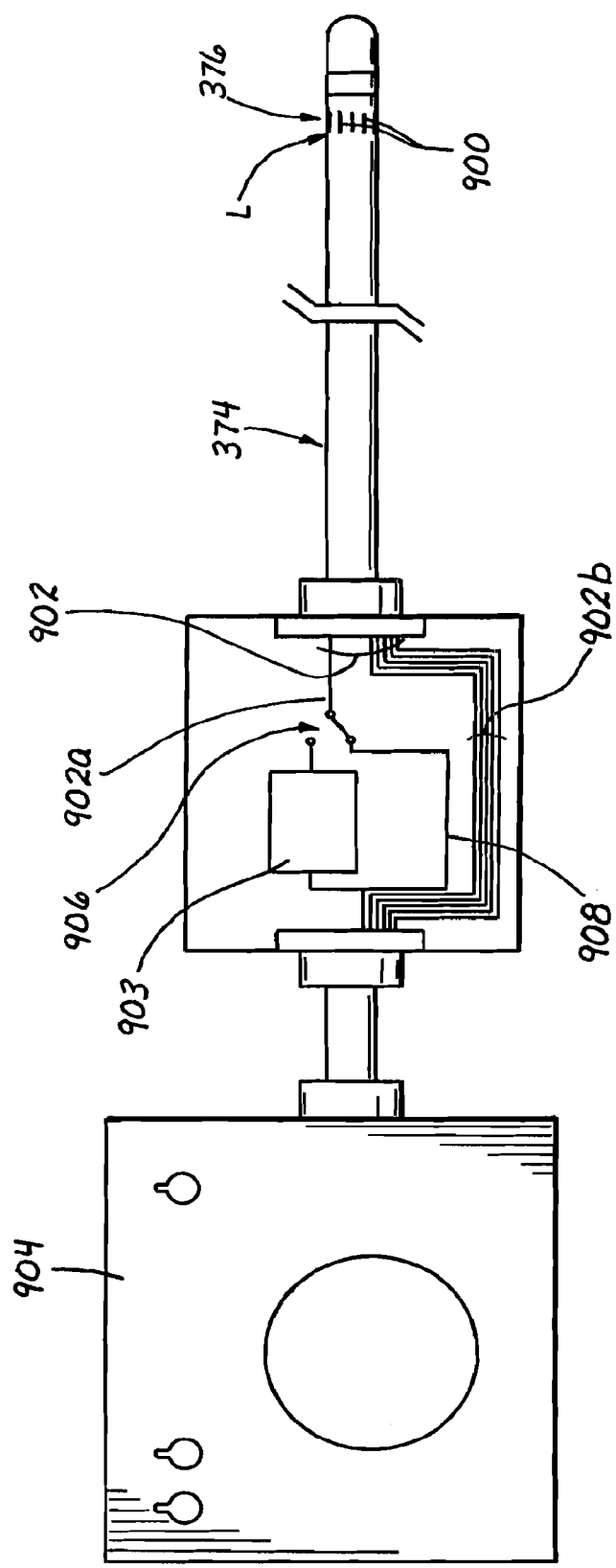
FIG. 4*l* is an exploded perspective view of a modified passageway-forming catheter, and a modified phased-array IVUS catheter useable in conjunction therewith to effect precise rotational positioning of the passageway-forming catheter.

The following detailed description and the accompanying drawings are provided for the purpose of describing and illustrating presently preferred embodiments of the invention only, and are not intended to limit the scope of the invention in any way.

It is to be appreciated that the individual elements and components of each of the embodiments described herebelow may be individually or collectively incorporated into each of the other embodiments capable of receiving or incorporating such element(s) or component(s), and no effort has been made to exhaustively describe all possible permutations and combinations of the inventive elements and components described herein.

i. Torqueable Introducer Sheath

Referring specifically to FIGS. 1-1g, the present invention includes a torqueable introducer sheath 10 comprising an elongate pliable tubular sheath body 12 having a proximal end PE and a distal end DE. The tubular sheath body 12 comprises a proximal segment 14, a medial segment 16 and a distal segment 18. A hollow lumen 20 extends longitudinally through the tubular sheath body 12, such hollow lumen 20 being defined by an inner luminal surface 22. A proximal hand piece or connector assembly 24 may be mounted on the proximal end PE of the sheath body 12 to facilitate manipulation of the proximal end PE of the sheath body 12 and to receive and register against the hand piece 26 of any catheter which is inserted through the torqueable introducer sheath 10.

A tubular catheter engaging member 28 is formed or mounted within the lumen 20 of the distal segment 18 of the tubular sheath body 12. Such tubular catheter engaging member 28 has a lumen 30 which extends longitudinally therethrough. The lumen 30 may be of any non-cylindrical or nonuniform configuration, such as "pair shape" or "egg-shape," whereby the luminal surface or a portion thereof will engage and prevent rotation of the catheter inserted through the sheath. An example of a generally oval shaped lumen is shown in FIG. 1a.

A plurality of elongate reinforcement members 32, formed of wire, fibers or other suitable material, are disposed within the proximal and medial segments 14, 16 of the tubular sheath body 12. These reinforcement members 32 may be helically wound about the lumen 20 of the sheath body 12 to form an overlapping braid structure 34. Other structures, such as a coil structure, may also be used. In particular, such overlapping braid structure 34 may comprise two groups of individual elongate members 32 helically wound in opposite phase about the longitudinal axis LA of the tubular introducer sheath body 12, and at cross over points of such groups of elongate members 32, the individual elongate members 32 of one group will be alternately passed over and under the individual elongate members 32 of the other group, so as to provide a braid structure 34 which will impart enhanced structural integrity and torque transfer to the proximal 14 and medial 16 segments of the tubular sheath body 12. In some embodiments, the distal segment 18 may also be provided with the elongate members 32 and/or braided structure.

In embodiment of this sheath intended for coronary application, the individual elongate members 32 may preferably be formed of stainless steel of 0.001-0.005 inch diameter. Each group of elongate members 32 may consist of eight such stainless steel wire members in substantially parallel side-by-side relation to one another. The first and second groups of elongate members 32 will be helically wound about a tubular inner liner 36, in opposite phase such that the first and second groups of elongate members will repeatedly cross over each other. At locations whereat the groups of elongate members 32 cross over each other, each individual elongate member 32 of each group may be alternately threaded over and under the individual elongate members 32 of the other group, so as to provide an interwoven, braided structure 34 which will impart enhanced torqueability to the tubular sheath body 12. A tubular outer skin 15 is then formed over the wire braid structure 34 such that the wire braid structure 34 is captured or located between the tubular outer skin 15 and the tubular core member 36, as shown.

In at least some applications it may desirable to impart regionalized differences in rigidity or hardness to the proximal and medial segments 14, 16 of the tubular sheath body 12. In this manner, the outer skin 15 of the proximal portion 14 may be formed of material which is more rigid or greater in hardness than that of the outer skin 15 of the medial portion 16. For example, the outer skin 15 of the proximal portion 14 may be formed of thermoplastic, elastin (e.g., Pebax, polyurethane, silicone, polyester) or thermoset elastomer (e.g., polyurethane or flexibly epoxy) (e.g., Pebax) having a Shore D hardness of 60-72 while the outer skin 15 of the medial portion 16 may be formed of polymeric material (e.g., pebax) having a lesser hardness, such as a 40-60 Shore D hardness on the shore D scale. The outer skin 15 of the distal portion 18 may preferably have a Shore D hardness in the range of 30-40. The relative lengths and hardness of the inner liner 36 and outer skin 15 may be varied to adjust the overall stiffness of the catheter and the locations of the transition areas between the proximal 14, medial 16 and distal 18 segments of the sheath 10.

In the preferred embodiment, shown in the drawings, the inner liner is formed of polytetrafluoroethylene (PTFE) of consistent hardness from the proximal end PE to the distal end DE of the tubular sheath body 12.

With reference to FIGS. 1f-1g, one type of passageway-forming catheter 40 which is useable in conjunction with the torqueable sheath 10 comprises an elongate pliable catheter 40 having an irregular cross sectional configuration defining an upper portion 42 through which a tissue-penetrating element 46 may pass and a lower portion 44 through which an imaging catheter (e.g., an IVUS catheter) may pass.

A tissue-penetrating element 46 of the type previously described in U.S. patent application Ser. No. 08/730,327 is advanceable out of the distal end DE of the upper catheter portion 42 such that the tissue penetrating element 46 will diverge laterally from the longitudinal axis LA of the catheter device 40. In this manner, the tissue-penetrating element 46 will pass through the wall of a blood vessel wherein the distal portion of the catheter device 40 is positioned so as to create an extravascular passageway extending from the blood vessel to another blood vessel or other extravascular target location.

As shown in FIG. 1g, when the catheter 40 is advanced through the torqueable introducer sheath 10, the upper portion 42 of the catheter body will engage the smaller diameter side of the lumen 30 of the catheter engagement member 28, while the relatively large diameter lower catheter portion 44 will engage the opposite end of such lumen 30, and the passageway-forming catheter 40 will be thereby prevented by the catheter engaging insert 28 from rotatably moving relative to the tubular body 12 of the sheath 10. In this manner, the operator may manually grasp the proximal connector 24 and may apply rotational force to the proximal connector 24, such that the rotational force will be transmitted through the tubular sheath body 12 so as to cause the distal segment 18 of the tubular sheath body 12 to rotate in a substantially one to one (1:1) relation to the proximal connector 24. In this manner, the torqueable introducer sheath 10 will cause the catheter 40 which has been inserted through the sheath 10 to rotate in conjunction with the sheath 10, irrespective of whether the body of the catheter 40 has sufficient structural integrity to be capable of transmitting torque from its proximal end to its distal end. This construction allows the use of a passageway-forming catheter 40 which is of relatively small diameter and formed of pliable or subtle material, while the torqueable sheath 10 may be of stronger and less pliable material capable of transmitting torque and acting as guide for insertion of the catheter 40. Additionally, the catheter engaging insert 28 may be positioned at or near the distal end of the sheath 10 so as to transmit torque to the catheter 40 at a location at or near its distal tip, thereby eliminating torque or rotational stress on the majority of the catheter shaft and eliminating the potential for kinking or buckling of the small diameter, pliable catheter body. In this manner, the use of the sheath 10 of the present invention in conjunction with the catheter 40 provides for the maintenance of precise rotational control of the distal portion of the catheter 40.

ii. Anchorable Guide Catheter

Referring to FIGS. 2-2b' there is provided an anchorable guide catheter which is useable in conjunction with i) an imaging catheter such as a commercially available IVUS catheter (e.g., 29 French Ultra-Cross available from Boston Scientific, 27 Orleans Dr., Sunnyvale, Calif.) and ii) a transvascular passageway forming catheter, one example of which is shown in FIGS. 3a-3d of this application and other examples of which are described in U.S. patent application Ser. Nos. 08/730,327 and 08/730,496.

The anchorable guide catheter 50, comprises a pliable tubular catheter body 52 having a proximal end PE and a distal end DE. First and second lumens 54, 56 extend longitudinally through the catheter body 52. An opening 58 is formed in one side of the catheter body 52, so as to provide an opening into the first lumen 54. A pressure exertive member such as a balloon 59 or other projectable apparatus such as a moveable foot, is mounted on the catheter body 52 at a location laterally opposite the location of the opening 58. An inflation fluid aperture 60 is formed in the sidewall of the catheter body 52 between the balloon 58 and the second lumen 56 such that balloon inflation fluid may pass into and out of the balloon 59, through the second lumen 56.

A proximal connector assembly 62 is mounted on the proximal end PE of the catheter body 52. Such proximal connector assembly 62 has a side arm port 64 in communication with the second lumen 56 such that balloon inflation fluid may be injected or withdrawn through the side arm port 64 to cause alternate inflation and deflation of the balloon 59. Also, the proximal connector assembly 62 has a proximal port 66 through which any elongate member of suitable size and configuration, such as the imaging (IVUS) catheter, a passageway forming catheter 40, or other catheters equipped for introducing channel connectors, channel sizers, lumen blockers, etc. as described in Applicant's earlier-filed U.S. patent application Ser. Nos. 08/730,327 and 08/730, 496, may be advanced through the first lumen 54 of the catheter body 52. The first lumen 54 of the catheter body 52 may be of a shape or configuration which is analogous to one or both of the catheters which are to be inserted through the first lumen 54 such that when such IVUS catheter, passageway forming catheter 70 or other elongate member 15 inserted into the first lumen 54, the outer surface(s) thereof will engage the inner surface of the first lumen 54 such that the IVUS catheter, passageway forming catheter 70 or other elongate member will be prevented from rotatably moving relative to the body of the catheter 52, and the operator will thereby maintain precise control over the rotational orientation of these apparatus. In particular, as shown in FIGS. 2b-2c, the first lumen 54 may have an inner lumenal surface 64 of a "D" shape.

Referring to FIGS. 3a-3d, a particular passageway forming catheter 70 which is useable in conjunction with the anchorable guide catheter 50 may comprise a pliable catheter body 72 having at least a distal portion 74 having a generally D-shaped outer surface 76 which is of substantially the same size and configuration as the D-shaped luminal surface 64 of the first lumen 54. A tissue penetrating element 78 extends through the pliable catheter body 72 and is connected to a trigger 80 formed on the proximal hand piece 82 of the catheter device 70 such that, when the trigger 80 is actuated, the tissue penetrating element 78 will pass out of a side opening 80 formed in the D-shaped portion of the catheter body 72 such that the tissue penetrating element 78 will diverge laterally from the longitudinal axis LA of the catheter body 72, in this manner, the tissue penetrating element 78 may be utilized to form an extravascular passageway which extends through the wall of the blood vessel into which the catheter 70 is inserted, to another blood vessel or other target location within the body.

Referring back to FIGS. 2a-2c', the anchorable guide catheter 50 is initially inserted into the vasculature and advanced to a position where the distal end DE of the balloon catheter body 52 and side opening 58 are located adjacent the location at which it is desired to form an extravascular passageway. An imaging catheter 80, such as an IVUS catheter, is inserted through the proximal port 66, and is advanced through the first lumen 54 until the imaging catheter 80 is in a position relative to the side opening 58 of the catheter body 52 to provide an image of anatomical structures located in alignment with such side opening 58. Thereafter, the guide catheter body 52 may be manually rotated until the image received through the imaging catheter 58 indicates that the opening 58 is directly aligned with the location at which the extravascular passageway is to be formed. In this regard, the catheter body 52 is of a torqueable construction, and may have the same dual-layer braided construction as described hereabove with respect to the torqueable sheath 10. In this manner, the anchorable guide catheter 50 may be manually rotated by the operator to effect precise rotational positioning of the opening 58 of the balloon anchorable guide catheter within the vasculature or other luminal anatomical structure within which the guide catheter 50 is inserted.

After the opening 58 of the balloon anchorable guide catheter 50 has been precisely rotationally positioned so that a passageway forming catheter 70 subsequently inserted through the guide catheter 50 will be appropriately aimed at the target anatomical location, the balloon 59 of the guide catheter 50 will be inflated (or the other pressure exertive member will be actuated) to engage the surrounding luminal anatomical wall and to hold the distal portion of the guide catheter 50 in substantially fixed longitudinal and rotational position/orientation. In this regard, the material in which the balloon 59 is formed may be frictionally textured or coated with adhesive or otherwise modified with a friction producing outer surface to enhance its friction against the luminal wall. In this manner the balloon 59 will soundly engage the surrounding luminal wall to hold the distal portion of the guide catheter 50 in fixed position.

Thereafter, the imaging catheter 80 will be extracted from the first lumen 54, and a passageway-forming catheter such as that shown in FIGS. 3a-3d and described hereabove, will then be inserted through the lumen 54. The passageway forming catheter 70 may be advanced until the distal end DE of the passageway forming catheter body 72 abuts against the distal end surface 82 of the first lumen 54 of the guide catheter 50. When so inserted, the D-shaped outer surface 76 of the distal portion 74 of the passageway forming catheter body 72 will be in abutment with the D-shaped luminal surface 64 of the first lumen 54 of the guide catheter body 52, as shown in FIG. 2c'. In instances where the proximal portion (i.e., that portion proximal to the distal portion 74) of the passageway forming catheter body 72 is not of the same D-shaped configuration, such proximal portion may simply reside within the D-shaped first lumen 54 in the manner shown in FIG. 2b. Thus, it is not necessary that the entire length of the passageway-forming catheter body 72 have the D-shaped outer surface 76, but only that a distal portion 72 thereof have the D-shaped outer surface 76 so as to frictionally engage the D-shaped luminal surface 64 of the first lumen 54 in the manner shown.

Because the anchoring balloon 59 has been inflated, the guide catheter body 52 will be prevented from rotating within the vasculature and will be held in a substantially fixed rotational orientation such that the side opening 58 is in direct alignment with the other blood vessel or target location to which the extravascular passageway is to extend. Thus, after the passageway-forming catheter 70 has been inserted into the first lumen 54 in the above-described manner, the triggering member 80 may be actuated to cause the tissue penetrating element 78 to pass out of the passageway forming catheter body 72, through the side opening 58 of the guide catheter, through the wall of the blood vessel in which the guide catheter 50 is located, and into another blood vessel or other extravascular target location. In some embodiments, the tissue penetrating element 78 may comprise a tubular member having a guidewire lumen 81 extending longitudinally therethrough. When such guidewire lumen 81 is present, a guidewire 79 may optionally be advanced through the tissue penetrating element 78 and into the other blood vessel or extravascular target location, after the tissue-penetrating element 78 has been advanced thereinto. After such guidewire 79 has been advanced into the other blood vessel or extravascular target location, the tissue penetrating element 78 may be retracted into the body of the passageway forming catheter 70, and the passageway forming catheter 70 and balloon anchorable guide catheter 50 may be extracted from the body, leaving the guidewire 79 in place to guide other devices or operative instruments through the newly created extravascular passageway.

iii. Passageway-Forming Catheter Device Having Torqueable Proximal Portion

FIGS. 4a-4e show another passageway-forming catheter device 100 of the present invention, which generally comprises an elongate catheter body 102 with definable proximal 104, medial 106 and distal 108 segments of varying flexibility and torque strength.

The proximal segment 104 and medial segment 106 of the catheter body 102 incorporate reinforcement members, such as a reinforcement member braid 110, which will impart structural integrity to the proximal segment 104 and medial segment 106, and will enhance the ability of the proximal segment 104 and medial segment 106 to transmit torque from the proximal end of the catheter body 102. In some embodiments, the distal segment 108 may also incorporate such reinforcement members and/or braid 110. The reinforcement members and braid may be similar to or the same as that described in detail hereabove in reference to FIG. 1.

As shown in FIG. 4a, the proximal segment 104 may be of greater diameter than the medial segment 106. In this manner, the proximal segment 104 may comprise a cylindrical, dual lumen core member 140a of a first diameter $D_1$ about which the reinforcement members or wire braid 110 are wrapped. An outer jacket 142a is then formed about the reinforcement members or wire braid 110, as shown in FIG. 4b.

The mid-portion 106 comprises a cylindrical core member 140b of diameter $D_2$, about which the reinforcement members or wire braid 110 are wrapped. A cylindrical outer jacket 142b is also formed about the mid-portion 106 of the catheter body 102, and is continuous with the outer surface of the distal portion 108, as shown in FIG. 4a.

It would be appreciated that the individual portions or members which make up each segment of 104, 106, 108 of the catheter body 102 may be formed of materials which have different physical properties (e.g., hardness, flexural properties, etc.) so as to bring about the desired regionalized variations in pliability and torque strength the catheter body 102. For example, in a presently preferred embodiment, the cylindrical core member 140a of the proximal portion 104 is formed of a polymer material of a first hardness (e.g., Pebax of 63E Shore Hardness) and the cylindrical core member 140b of the mid-portion 106 is formed of a polymer material having a different hardness (e.g., Pebax of 40D Shore Hardness). The outer jacket 142 a of the proximal portion 104 is formed of another polymeric material having yet a different hardness (e.g., Pebax 70D Shore Hardness) and the outer jacket 142d of the mid-portion 106 is formed of polymeric material having the same or similar hardness of that of the mid-portion 106 (e.g., Pebax of 40D Shore Hardness) other polymeric materials which may be used to form portions or members of the catheter body 102 include nylon, polyurethane, polyester, polyvinyl chloride (PVC) etc.

The catheter body 102 has a bottom portion BP and an upper portion UP. A curved or slanted frontal surface is formed on the distal end of the upper portion UP.

A first lumen 130 extends longitudinally through the catheter body from the proximal end to the distal end of the upper portion of the catheter body, and terminates distally at the distal outlet aperture 134.

A second lumen 132 also extends longitudinally through the catheter body from the proximal end thereof to a closed end wall or plug at the distal end of the lower portion LP of the catheter body 102. A proximal connector 136 is mounted on the proximal end of the catheter body. A proximal connector 136 has a proximal end port 134 and a side arm port 138. The proximal end port 134 is in communication with the first lumen 130 of the catheter body 102, and the side arm port 138 is in communication with the second lumen 132 of the catheter body 102. A tissue-penetrating element 150 extends through the first lumen 130. This tissue penetrating element 150 may be any suitable type of tissue penetrating element member, device, or flow of energy, as previously described in U.S. patent application Ser. No. 08/730,324, of which this application is a continuation-in-part. In embodiments wherein the tissue penetrating element 150 is an advanceable member or device, a handpiece of the type shown in FIG. 3a-3b may be mounted on the proximal end port 134 such that the trigger 80 is connected to the tissue penetrating element 150 and is useable to alternately advance and retract the tissue penetrating element 150, out of/into the outlet aperture 134.

An imaging catheter, such as an intravascular ultrasound (IVUS) catheter may be inserted through one of the ports 134, 138 of the proximal connector 136 connected to the second lumen 132. In this manner the imaging catheter (IVUS) may be advanced through the second lumen 132 such that a distal portion of the imaging catheter extends into or out of and beyond the distal extent of the second lumen 132, thereby placing the imaging transducer or image receiving apparatus at a vantage point which is distal to the outlet aperture 134. Such imaging catheter may then be utilized to image anatomical structures which are situated adjacent to in the vicinity of the outlet aperture 134, and to view the passage of the tissue-penetrating element 150 out of the outlet aperture 134 and through/into the adjacent anatomical structure.

iv. A Deflectable Catheter System for Forming Extraluminal Passageways

Figure 7:
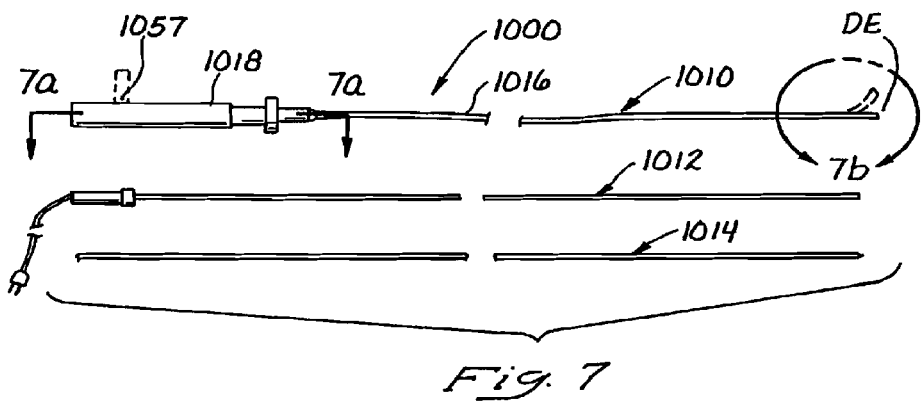
FIG. 7 is a perspective view of a deflectable-tipped passageway forming catheter system of the present invention which comprises a) a deflectable tipped catheter; b) an imaging component which is advanceable through the deflectable-tipped catheter and c) a tissue-penetrating component which is passable through the deflectable-tipped catheter.
Figure 7A:
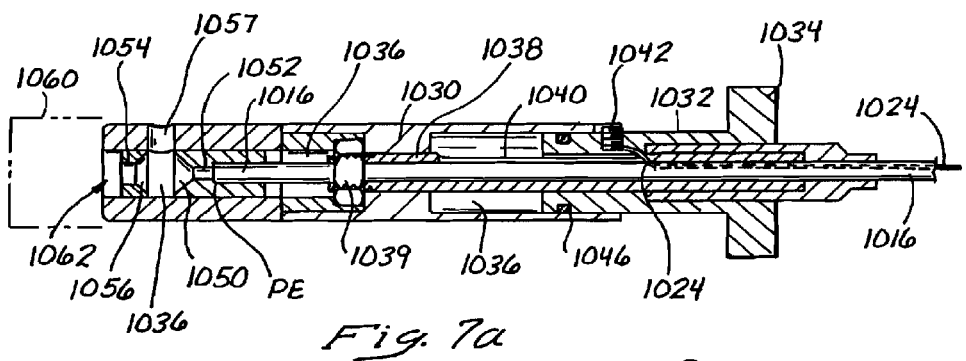
FIG. 7a is a longitudinal sectional view of the handpiece portion of the deflectable tipped portion of FIG. 7.
Figure 7B:
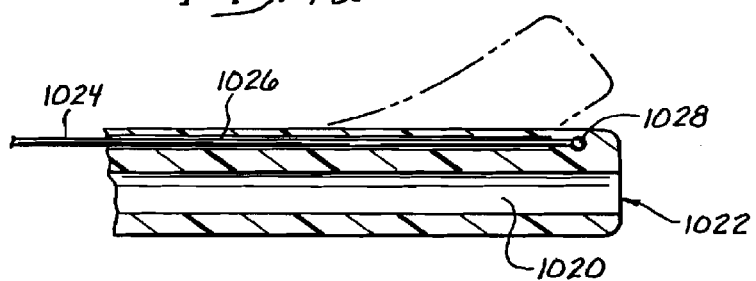
FIG. 7b is a longitudinal sectional view of the distal portion of the deflectable-tipped catheter of FIG. 7.

FIGS. 7-7b show another type of catheter system which may be utilized to form interstitial passageways between a luminal anatomical structure (e.g., a blood vessel) within which the catheter is positioned and another target anatomical location (e.g., another blood vessel, chamber of the heart, organ, tumor, etc.).

As shown in FIG. 7, the system 1000 comprises a deflectable tipped catheter 110 which is useable in combination with an imaging catheter 112 (e.g., an IVUS catheter) and a tissue penetrating element 114 (e.g., a sharp-tipped elongate member, or a flow of tissue-penetrating energy).

The deflectable tip catheter 110 comprises an elongate pliable catheter body 1016 having a deflectable distal end DE and a proximal end PE which is connected to a handpiece 1018.

A presently preferred construction of the handpiece 1118 is shown in FIG. 7a, and a presently preferred construction of the distal end DE of the catheter body 1016 is shown in FIG. 7b.

A working lumen 1020 extends longitudinally through the catheter body 1016 and through an opening 1022 in the distal end DE of the catheter body 1016. A secondary lumen 1026 extends longitudinally through the catheter body 1016, at an off center location along one side of the catheter body. Such secondary lumen 1026 terminates within the catheter body near the distal end thereof, and is thus a blind lumen. A pull wire 1024 extends longitudinally through the secondary lumen 1026 and the distal end 1028 of the pull wire 1024 is anchored or attached to the catheter body at a location within the catheter body, near the distal end thereof. The pull wire 1024 is axially moveable within the secondary lumen 1026 such that, when the pull wire 1024 is retracted in the proximal direction, it will cause the distal end DE of the catheter body 1016 to deflect in lateral direction, toward the side on which the secondary lumen 1026 is formed, as shown in FIG. 7b.

The handpiece 1018 comprises a rear body portion 1030 and a forward body portion 1032 a knob 1034 is formed on the forward body portion 1032. The proximal end of the forward body portion 1032 is received within an inner bore 1036 of the rear body portion 1030 and is slidably retractable and advanceable within such bore 1036. A tubular member 1038 is positioned axially within the bore 136 of the rear body portion 1030 and extends through a portion of the forward body portion 132 as shown. This tube member 1038 is attached and anchored within the handpiece 1018 by way of a nut 1039. The catheter body 1016 extends through the tubular member 1038 and the proximal end PE of the catheter body 1016 is anchored within the rear body portion 1030, as shown. A slot 1040 is formed in the side of the tube member 1038. The pull wire 1014 extends through a small hole formed in the side of the catheter body 1016 within the forward body portion 1032 and through the slot 1040. The proximal end of the pull wire 1024 is attached to a set screw 1042 mounted in the side of the forward body portion 1032. An 0-ring 1046 is mounted within an annular groove formed in the proximal portion of the forward body portion 1032 such that the 0ring will ride against the inner surface of the bore 1036 of the rear body portion 130 as the forward body portion 1032 is advanced and retracted therewithin.

In operation, when it is desired to cause the distal end DE of the catheter body 1016 to deflect laterally, the operator will grasp the knob 1034 of the forward body portion 1032 and will proximally retract the forward body portion 1032 into the bore 1036 of the rear body portion 1030, while the catheter body 1016 remains axially stationary due to its affixation to the proximal body portion 1030. In this manner, the pull wire 1024 will be proximally retracted within the secondary lumen 1026 and will cause the distal end DE of the catheter body 1016 to deflect in the desired lateral direction, as shown. Such deflection of the distal end DE of the catheter body 1016 may be utilized to cause the distal end outlet aperture 1022 to be specifically directed or aimed at the luminal wall of a luminal anatomical structure within which the catheter body 1016 is inserted.

A first frusto conical bore 1050 is formed within an insert member 1052 located in the rear body portion 1030, and within which the proximal end PE of the catheter body 116 is extended. This frusto conical bore 1050 leads directly into the proximal end of the working lumen 1020 of the catheter body 1016 and will facilitate distally directed advancement of a guidewire, imaging catheter 1012, tissue penetrating element 1014, or other elongate apparatus through the main lumen 1020 of the catheter body 1016.

Another insert member 1054 having an opposite redirected frusto conical bore 1056 is also mounted within the bore 1036 of the rear body portion 1030, proximal to the first insert member 1052. This oppositely directed frusto conical bore 1056 will serve to guide and center the proximal end of a guidewire or similar elongate apparatus over which the catheter body 116 may be advanced such that it passes out of the proximal end PE of the catheter body 116.

Optionally, a hemostasis valve and/or gripping apparatus 1060 may be mounted on the proximal end of the rear body portion 130, immediately adjacent the proximal end opening 1062 of the bore 136 through which the guidewire(s), imaging catheter 1012, tissue penetrating element 1014 or other elongate apparatus may be passed.

In a preferred mode of operation, the catheter body 1016 is initially inserted into a luminal anatomical structure such that the distal end DE of the catheter body 1016 is located generally adjacent a site at which an interstitial passageway is to be formed through the wall of the luminal anatomical structure within which the catheter body 1016 is positioned. The imaging catheter 1012 (e.g., an IVUS catheter) is advanced through the proximal opening 1062, through the frusto conical bore 1050, and through the working lumen 1020 of the catheter body 1016 until the transducer or image-receiving element of the imaging catheter 1012 is appropriately positioned to image the side wall of the luminal anatomical structure within which the catheter body 1016 is inserted and/or the target anatomical location to which the interstitial passageway is desired to extend. In many instanced, this will require that a distal portion of the imaging catheter 1012 protrudes slightly out of and beyond the distal end opening 1022 of the working lumen 1020. With the image catheter 1012 in its operative position, it may be utilized to precisely locate the distal end DE of the catheter body 1016 in the desired longitudinal location and rotational orientation which will cause the distal end opening 1022 to be in alignment with the specific site on the wall of the luminal anatomical structure through which the passageway is to be formed. In this manner, one or more imageable markers or other aiming/positioning systems as described in this patent application or in applicant's related patent applications may be incorporated into the system 1000 to facilitate precise aiming and positioning of the distal end DE of the catheter body 1016.

After the distal end DE of the catheter body 1016 has been longitudinally and rotationally positioned/oriented, the imaging catheter 1012 will be extracted and removed, and the tissue-penetrating element 1014 will then be advanced through the proximal opening 1062, through the frusto conical bore 1050, and through the working lumen 1020 until the tissue-penetrating element is near the distal end opening 1022 but still contained within the working lumen 1020. Thereafter, the operator will grasp the knob 1034 of the handpiece 1018 and will retract the forward body portion 1032 of the handpiece rearwardly, into the rear body portion 1030. This will cause the pull wire 1024 to retract and will cause the distal end DE of the catheter to become laterally deflected such that the distal end opening 1022 is positioned in direct alignment with the site on the wall of the luminal anatomical structure through which the passageway is to be formed. Thereafter, the tissue-penetrating element 1014 will be further advanced out of the distal end opening 1022 of the catheter body 1016, through the wall of the luminal anatomical structure, and through any intervening tissue, until the tissue-penetrating element 1012 emerges into the intended target anatomical location.

Thereafter, the tissue-penetrating element 1014 may be retracted through the working lumen 1020 and removed.

Thereafter, one or more secondary apparatus (e.g., channel connector delivery catheters, channel enlarging/modifying catheters, blocker catheters, etc.), may be advanced through the working lumen 1020 of the catheter to perform any desired modifications of the interstitial passageway or delivery of ancillary devices to facilitate flow of blood or biological fluids through the passageway, as desired.

Thereafter, when the procedure has been completed, the operator may again grasp the knob 1034 of the forward body portion 1032 and may distally advance the forward body portion to its original position, thereby allowing the distal end DE of the catheter body 1016 to return to its substantially straight, non-deflected configuration.

Those skilled in the art will appreciate that various modifications or changes may be made to the above-described system 1000 without departing from the intended spirit and scope of the invention. For example, although the preferred embodiment has been shown with a single working lumen 1020 extending through the deflectable catheter 1010, a plurality of such lumens may be formed to allow multiple components (e.g., the imaging catheter 112 and the tissue penetrating element 1014 and/or a guidewire (not shown)) to extend through the catheter body 1016 simultaneously. However, in many applications it will be desirably to minimize the diameter of the catheter body 1016 and to maximize its pliability or flexibility, thereby rendering it desirable to utilize a single lumen 1020 in such applications.

Optionally, a side port 1057 may be formed in the rear body portion 1030 to permit infusion/withdrawal of fluid through the working lumen 1020 of the catheter 1000.

V. Markers and Related Apparatus for Positioning/Aiming the Passageway Forming Catheters FIGS. 4d-6c show various markers and other apparatus which may be incorporated into any of the passageway forming catheters described in this patent application or any other suitable catheter, to provide a means for visually determining (e.g., by intracorporeal imaging such as intravascular ultrasound, or by extracorporeal imaging such as fluoroscopy) the precise positioning and rotational orientation of the distal portion of the catheter and/or for precisely aiming the tissue-penetrating element so that it will create the desired interstitial passageway as it is passed out of the passageway-forming catheter.

In particular, FIGS. 4d-4e show markers which are particularly suitable for use on passageway-forming catheters which have a stepped or slanted distal end configuration, such as that of the torqueable catheters shown in FIG. 4a. The remaining showings of FIGS. 4g-6c show markers and guidance/aiming apparatus which are useable with passageway-forming catheters which have various distal end configuration.

Referring to FIG. 4d, there is shown a distal portion of a passageway-forming catheter 100 hereupon a generally U-shaped marker 180 is mounted on the upper surface of the lower catheter body, distal to the tissue-penetrating outlet opening 134. The longitudinal midline of the marker 180 is in alignment with the path which will be followed by the tissue penetrating element 150 as it is advanced out of the opening 134 in the catheter 100. In this manner, an imaging apparatus such as an IVUS catheter positioned within the lower catheter body portion at a vantage point distal to the distal end of the tissue-penetrating element outlet opening 134, may be utilized to ensure that the marker 180 is in direct alignment with the target tissue prior to advancement of the tissue penetrating element 150 out of the opening 134.

FIG. 4e shows a passageway forming catheter 100 having a marker strip 182 mounted on the upper portion of the lower catheter body, distal to the location of the tissue-penetrating element outlet opening 134. This marker strip 182 creates an image artifact which extends out radially to allow *point* in a specific direction which corresponds to the path of the tissue penetrating element. The longitudinal midline of this marker strip 182 is in alignment with the path which will be followed by the tissue-penetrating element 150 as it passes out of the opening 134. In this manner, an imaging apparatus such as an IVUS catheter positioned within the lower catheter body portion at a vantage point distal to the distal end of the tissue-penetrating element outlet opening 134, may be utilized to ensure that the marker strip 184 is in direct alignment with the target tissue, prior to advancement of the tissue penetrating element 150 out of the opening 134.

FIG. 4f shows a wire marker 186 mounted on the distal portion of a passageway-forming catheter 100 which has an optional imaging window 101 formed in the lower catheter body, distal to the tissue-penetrating element outlet opening 134. The details of this imaging window were previously described in applicant's earlier-filed U.S. patent application Ser. No. 08/730,496. The wire marker 186 comprises a single, elongate wire which is attached at its opposite ends, to the proximal and distal boarders of the window 101. The elongate wire marker 186 is preferably in the center of the window 101 and in alignment with the path which will be followed by the tissue penetrating element 150 as it is advanced out of the opening 134 in the catheter 100. In this manner, an imaging apparatus such as an IVUS catheter positioned within the lower catheter body portion so as to obtain an image through the imaging window 101, may be utilized to ensure that the marker wire 186 is in direct alignment with the target tissue prior to advancement of the tissue penetrating element 150 out of the opening 134.

FIG. 4g shows another passageway-forming catheter 100' which has an imaging lumen 300 through which an imaging catheter may be advanced, and a working lumen 302 through which a tissue-penetrating element 150 may pass, such working lumen 302 terminating distally in an outlet opening 134 formed in the side of the catheter 100' at a spaced distance proximal to the distal end of the imaging lumen 300, as shown. A pliable distal tip member 189 is mounted on the distal end of the catheter 100', and the imaging lumen 300 extends through such tip member 189 and terminates in a distal opening formed therein. Additionally, a hollow passageway 191 extends longitudinally through such tip member 189 in direct alignment with the main portion of the working lumen 302. An imagable marking wire member 188, preferably formed of a combination of platinum and stainless steel, extends through the hollow passageway 191 in the tip member 189, and is surrounded laterally by a gap or space 193 within such passageway 191, as shown. The proximal end of this wire member 188 is embedded in a mass of imagable material 190 located within the body of the catheter 100'. Such mass of imagable material 190 is preferably a mixture of tungsten and a plastic (e.g., Pebax) or platinum. The distal end of the wire member 188 protrudes out of and beyond the distal end of the catheter body, as shown.

FIGS. 4h-4h' show another passageway-forming catheter 100" comprising an elongate pliable catheter body having an imaging lumen 300 and a working lumen 302. An imaging apparatus, such as IVUS catheter, is advanceable through the imaging lumen 300. A tissue penetrating element (not shown) is passable through the working lumen 302 and out of the outlet aperture 134. A marker wire lumen 314 extends through a distal portion of the catheter 100" between a proximal opening 316 formed in the upper wall of the imaging lumen 300, and a distal outlet aperture 318 formed in the distal end of the catheter 100", above the distal end outlet 320 of the imaging lumen 300. A marker wire 310 is disposed within the imaging wire lumen 314. A proximal bulb 322 is formed on the proximal end of the marker wire 310, and an optional distal bulb 324 may be formed on the distal end thereof. Initially, the marker wire 310 is fully retracted into the marker wire lumen 314 such that its distal tip and any distal bulb 324 is wholly contained within the body of the catheter 100", and with the proximal bulb 322 protruding slightly into the imaging lumen 300. The marker wire may be spring loaded or otherwise biased to this proximally retracted position. Thereafter, when an IVUS catheter is advanced through the imaging lumen 300, the distal end of the advancing IVUS catheter will drive the proximal bulb 322 of the marker wire 310 into a proximal cavity 326 formed at the proximal end of the marker wire lumen 314, thereby advancing the marker wire 310 such that a portion of the marker wire and its distal bulb 322 extends out of the distal end outlet aperture 318 and protrudes beyond the distal end of the catheter 100", as shown in FIG. 4h. The distal bulb 322 and a longitudinal axis of the marker wire 310 are in direct with the path which will be followed by a tissue-penetrating element (not shown) as it passes out of the outlet aperture 134. Thus, when the distal bulb 322 of the distally advanced marker wire 310 is in direct alignment with the target tissue on the image received by the IVUS catheter, such will ensure that when the tissue penetrating element is advanced out the outlet aperture 134, it will be properly aimed and will advance into the target tissue, as desired.

FIGS. 4i and 4i' show another passageway-forming catheter 100''' having an imaging lumen which terminates in a distal outlet aperture 320 and a working lumen which terminates in a side outlet aperture 134. An imaging catheter, such as an IVUS is advanceable through the imaging lumen, and a tissue-penetrating element (not shown) is advanceable out of the side outlet aperture 134.

In the particular embodiment shown in FIG. 4*i*, an arcuate wire marker 330 is mounted on the distal end of the catheter 100''', in a generally horizontal plane, above the distal out end outlet 320 of the imaging lumen 300. This arcuate wire marker 330 may be imaged by the transducer of an imaging catheter which protrudes out of the distal end outlet 320, and a specific, region of the artifact or image produced by the arcuate wire marker 330 may be fused, aimed or aligned with the target tissue, taking into account the distance between the catheter 100 and the target tissue, thereby ensuring that when the tissue penetrating element (not shown) is advanced out of aperture 134 it will extend into the intended target anatomical location or tissue.

In the alternative embodiment shown in FIG. 4*i*', there is provided a 3-legged wire marker 332 mounted on the distal end of the catheter 100'''. Such 3-legged wire marker 332 comprises bottom legs 334 formed of single wire strands and an upper leg 336 formed of a single wire strand additionally having an outer wire coil formed therearound. The single wire strand and the outer wire coil may be formed of different materials. The upper leg 336 is in direct longitudinal alignment with the half which will be followed by the tissue penetrating element as it passes out of the side outlet aperture 134 of the catheter 100'''. In this manner, when an imaging catheter such as an IVUS is advanced out of the distal end opening 320 of the imaging lumen, it may be utilized to directly align the upper leg 336 of the three-legged wire marker 322 with the intended target tissue, thereby insuring that when the tissue penetrating element is passed out of the side outlet aperture 134, it will form the desired passageway into the target tissue.

FIGS. 4*j*-4*j*' show a passageway forming catheter 100''' having the same configuration as that of FIGS. 4*i*-4*i*', but wherein a deflectable wire marker 340 is mounted on the end of the catheter 100''', as shown. Such deflectable wire marker 340 preferably comprises a singe wire strand having an additional wire coil formed therearound. This deflectable wire marker 340 has a top end 342 which is attached to the body of the catheter 100''' at a site which is in direct longitudinal alignment with the side outlet aperture 134. When the deflectable wire marker 340 is in its non-deflected position (FIG. 4*j*) its bottom end 344 will protrude downwardly over the distal end outlet 320 of the imaging lumen 300. Thus, when an imaging catheter such as an IVUS catheter is advanced through the imaging lumen 300 and out of the distal end outlet aperture 320 it will abut against the bottom portion of the deflectable wire marker 340, thereby causing the deflectable wire marker 340 to assume a deflected position as shown in FIGS. 4*j*'. When the deflectable wire marker 340 is in such deflected position, the longitudinal axis of the deflectable wire marker 340 will be in direct alignment with the path which will be followed by the tissue penetrating element (not shown) as it is passed out of the side outlet aperture 134. In this manner, the imaging catheter (IVUS) may be utilized to directly align the longitudinal axis of the deflectable wire marker 340 with the target tissue, thereby insuring that when the tissue penetrating element is passed out of the side outlet aperture 134 it will form the desired interstitial passageway into the target tissue.

FIG. 4*k* shows the same tissue-penetrating catheter 100''' wherein a secondary guidewire lumen 348 extends longitudinally through the body of the catheter 100''', from a proximal aperture 350 formed in the distal curved surface of the working lumen 302 to a distal guidewire outlet aperture 352 formed in the distal end of the catheter body, as shown. In this embodiment, the tissue penetrating element 150' comprises an elongate member having a sharpened distal end and a hollow guidewire lumen extending longitudinally therethrough. A guidewire 356 is advancable through the guidewire lumen of the tissue penetrating element 150'. When the tissue penetrating element 150 is retracted into the working lumen 302 as shown in FIG. 4*k*, the guidewire 356 may be advanced out of the distal end of the tissue penetrating element 150, through the secondary guidewire lumen 348, wherein it will act as a marker which may be imaged by a imaging apparatus (e.g., an IVUS catheter) passed through the imaging lumen 300. The longitudinal axis of the guidewire 356, when positioned within the secondary guidewire lumen 348, will be in direct alignment with the path which will be followed by the tissue penetrating element 150 as it is advanced out of the side outlet aperture 134.

The showing of FIG. 4*k* also incorporates a separate image-enhancing means whereby energy (e.g., ultrasonic vibration) may be imparted to the tissue penetrating element 150' as it is advanced out of the side outlet aperture 134 to render the distal portion of the tissue penetrating element 150' more easily visible by the imaging apparatus (e.g., IVUS catheter) positioned in the imaging engage the wall of the imaging lumen 300 to prevent the phased array imaging catheter 374 from rotating within the imaging lumen 300. An electronic marker is formed within the circuitry of the phased array imaging catheter 374 so as to mark a desired location L which is in direct alignment with the outlet aperture 134 of the catheter 100''' when the phased array imaging catheter 374 is non-rotatably inserted into the imaging lumen 300. In this manner, the electronically marked location L may be placed in direct alignment with the target tissue viewed on the image received through the phased array imaging catheter 374, thereby insuring that the outlet aperture 134 is also in alignment with the target tissue. It should be appreciated, that as an alternative to internally or electronically marking the desired location L on the phased array transducer 376, various imagable markers may be formed on the body of the catheter 100''' to mark the rotation of the outlet aperture 134, examples of such imagable markers being described hereabove and shown in FIG. 4*d*-4*k*.

One example of an electrical system which may be utilized to electronically mark a desired location L on the image received from the phased array transducer 376 is shown, in schematic fashion, in FIG. 4*l*'. With reference to FIGS. 4I and 4I', the phased array transducer 376 of the phased array imaging catheter 374 has a plurality of individual crystals 900 formed at spaced-apart locations on the transducer 376. Wires 902 extend from each of the individual crystals 900 of the phased array transducer 376, through the body of the phased array imaging catheter 374 and out of the proximal end thereof. One of these individual wires 902*a* is separated from remaining wires 902*b*, and the remaining wires 902*b* extend directly into a monitoring console 904 which produces the viewable image from the phased array transducer 376. The selected wire 902*a* is connected to a switch 906. When the switch 906 is in its open position, the signal received from the selected wire 902*a* will be shunted through a bypass circuit 908 which rejoins the remaining wires 902*b* prior to entry into the monitoring console 904. In this manner, when the switch 906 is open, the signal received from the selected wire 902*a* will bypass the signal modifying apparatus 903 and will rejoin the signals received from the remaining wires 902*b* to provide an image on the image monitoring console 904 which is unchanged and unmarked. However, when the switch 906 is closed, the signal received from the selected wire 902*a* will pass through a signal modifying apparatus 903. This signal modifying apparatus 903 may simply be an open switch which terminate the signal, thereby providing a void in place of the image which would be displayed from the individual crystal 900 from which the selected wire 902*a* extends. Alternatively, such signal modifying apparatus 903 may be a saturation apparatus which will produce white noise, or a color imparting apparatus which will tint or color the image received from the selected wire 902*a*. In either case, the image which subsequently appears on the image monitoring console 904 from the selected crystal 900 from which the selected wire 902*a* extends will be visually discernable by the operator and will provide a marking of the desired location L on the phased array imaging transducer 976.

FIGS. 4*m* and 4*m*' the presently preferred embodiment comprising a catheter 100"" wherein a segment of the catheter body is cut away, with a plurality (e.g., (three (3)) struts 402, 404, 406 formed a connection between a proximal portion 408 of the catheter 100"" and a distal portion 410 thereof, so as to form an imaging cage wherein the imaging catheter (e.g., IVUS) may be positioned. The top strut member 404 is of elongate configuration, and it longitudinal axis is directly aligned with the side outlet screen which directly correlates to the path which will be followed by the tissue-penetrating element, such artifact (e.g., ray or streak) being useful to enable the operator to determine the precise path which will be followed by the tissue penetrating element. In other applications, the marker may be formed of material which is reflective of the energy form such that a bright spot or exaggerated area will appear on the image screen when such marker is surrounded by tissue or other matter which is less then totally reflective of the energy form. Thus, in addition to the above-described methods for modifying the markers by applying energy (e.g., ultrasound) to the body of the marker, the exact form of the image or artifact produced by the marker may also be altered or optimized by forming the marker of a particular material of varied acoustic impedance, ranging from air or fluid filled cavities, to solid materials, to produce a range of marker effects on the image produced.

FIG. 5 shows an alternative positioning-aiming system which is useable to facilitate precise positioning and aiming of the passageway forming catheter 100*a*. In this system, a signal emitting apparatus 500 is positioned in the target area (e.g., within a second blood vessel BV.sub.2) and a signal receiving apparatus 502 is mounted within the passageway-forming catheter 100*a* located within in a first blood vessel BV.sub.1. The signal emitting apparatus 500 comprises a signal emitting wire 504 having a tubular shield 506 surrounding the shaft of the wire such that only a distal portion 508 of the wire 504 extends out of the distal end of the shielding tube 506. The shielding tube 506 may comprise any suitable electromagnetic shielding material, and is preferably formed of a pliable plastic tube having an aluminum braid formed therein. Those skilled in the art will appreciate that the signal emitting wire 504 may be attached to an extracorporeally located signal generating apparatus capable of passing an electromagnetic signal through the wire 504. Such electromagnetic signal may be a 20 Khz signal.

The signal receiving apparatus 502 is preferably formed within the wall of the passageway forming catheter 100*a* laterally outboard of the working lumen 302 through which the tissue penetrating element is passed, and in direct alignment with the tissue penetrating element outlet aperture 134 formed in the side of the catheter 100*a*. Optionally, the catheter 100*a* may also include an imaging lumen 300 through which and imaging catheter (e.g., an IVUS catheter) may be passed. However, those skilled in the art will appreciate that in many applications the signal emitting apparatus 500 and signal receiving apparatus 502 will be operable to control the precise positioning and rotational orientation of the catheter 100*a*, and such imaging lumen 300 may be unnecessary.

The signal receiving apparatus 502 formed in the passageway-forming catheter 100*a* comprises a signal receiving wire 510 having a tubular shielding apparatus 512 formed therearound. The tubular shielding apparatus 512 surrounds the shaft of the receiving wire 510 and a short distal portion 514 of the receiving wire 510 extends out of and beyond the distal end of the tubular shield 512. The tubular shield 512 may be formed in the same manner as the above-described tubular shield 506 of signal emitting apparatus 500. The exposed distal portion 514 of the signal receiving wire 510 is located immediately adjacent, and in longitudinal alignment with the side outlet aperture 134. In this manner, an electro magnetic signal may be emitted through the signal emitting apparatus 500 after it has been positioned within the second blood vessel BV.sub.2 or other target tissue. The longitudinal positioning and rotational orientation of the passageway-forming catheter 100*a* inserted within the first blood vessel BV.sub.1 may then be adjusted until the signal received by the signal receiving apparatus 502 of the catheter 100*a* is at its peak intensity, thereby indicating that the exposed distal portion 514 of the receiving wire 510 has been positioned at its closest possible point to the exposed distal portion 508 of the signal emitting wire 504. This will ensure that the passageway forming catheter 100*a* is longitudinally positioned at the closest straight-lined point from the signal emitting apparatus 500 located within the second blood vessel BV.sub.2 or other target tissue, and that the catheter 100*a* has been rotated to a rotational orientation wherein the outlet aperture 134 is directly aimed at the signal emitting apparatus 500 located within the second blood vessel BV.sub.2 or other target tissue. It will be further appreciated by those skilled in the art that various types of energy-emitting signals may be utilized into, such that the signal emitting apparatus 500 located within the second blood vessel BV.sub.2 or target tissue is an "active" element and the signal receiving apparatus 502 associated with the passageway forming catheter 100*a* is a "passive" or receiving element. The types of signals which may be utilized include, but are not necessarily limited to, electromagnetic signals (as specifically described hereabove), sonic signals (e.g., doppler), ultrasonic signals, high intensity light, laser, radiofrequency, etc.

Figure 5A:
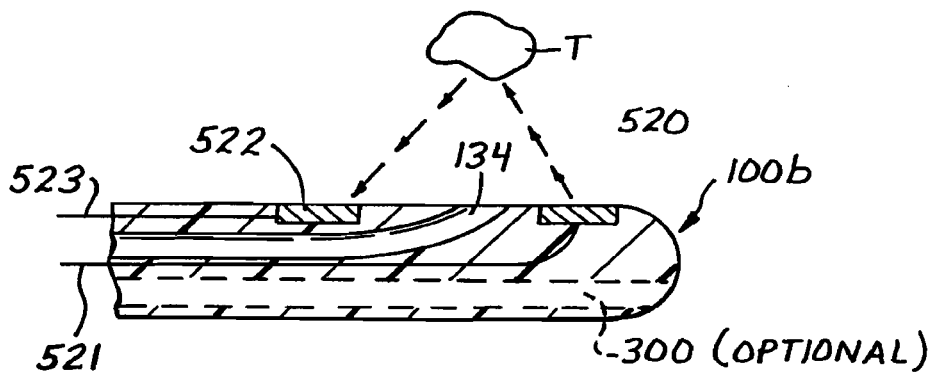
FIG. 5*a* is a partial longitudinal sectional view of a passageway-forming catheter of the present invention having an alternative aiming/positioning system formed thereon, such system comprising an active (emitting) component and a passage (receiving) component.

FIG. 5*a* shows another positioning/aiming system which is wholly incorporated into the passageway-forming catheter 100*b*. A signal emitting or "active" component 520, such as a piezoelectric crystal is mounted upon or formed within the catheter 100*b* so to emit a signal or flow of energy which will strike, enter or be reflected from the target tissue T. A passive or receiving apparatus, such as another piezoelectric crystal may be mounted at a second location within or upon the catheter 100*d* so as to receive a reflected signal or returning signal from the target tissue T. The position of the passive or receiving apparatus 522 relative to the active or emitting apparatus 520 is known, and may be utilized to precisely determine the longitudinal position and rotation orientation of the catheter 100b. In this manner, this positioning/aiming system may be utilized to effect precise longitudinal positioning and rotational orientation of the catheter such that when the tissue penetrating element is passed out of the outlet aperture 134, it will extend into the target tissue T, as desired. Those skilled in the art will appreciate that, as an alternative to the passive receiving apparatus 522, or in addition thereto, an optional imaging lumen 300 may extend through the body of the catheter 100b such that an imaging catheter (e.g., IVUS catheter or receiving catheter carrying the passive receiving apparatus 522 may be passed through such lumen 300 and utilized to alternatively or additionally facilitate the positioning and rotational orientation of the catheter 100b.

Figure 5B:
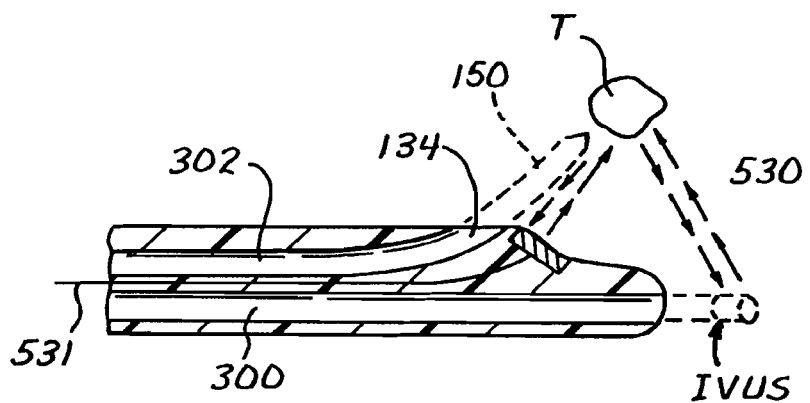
FIG. 5*b* is a partial longitudinal sectional view of another passageway-forming catheter of the present invention which incorporates another aiming/positioning system thereon, such system comprising an active (e.g., emitting) component mounted on the body of the catheter and an imaging catheter component (e.g., an IVUS catheter) advanceable through an imaging catheter lumen of the passageway-forming catheter to image the target tissue after the target tissue has been affected by energy received from the active (emitting) component.

FIG. 5b shows yet another alternative positioning/aiming system wherein a signal emitting crystal 530 is positioned on or within the catheter 100c so as to emit a signal (e.g., ultrasound or sound waves) in a direction which is specifically aligned with the path which will be followed by the tissue penetrating element as it passes out of the side outlet aperture 134 an imaging catheter. An imaging catheter (e.g., an IVUS catheter) positioned within the imaging lumen 300 is utilized to receive the signal from the crystal 530 after it has reflected from the target tissue T, thereby discerning the specific point of impingement X on the target tissue T where it is struck by the energy being emitted by the signal emitting crystal 530. In this manner, the imaging catheter positioned within the imaging lumen 300 may be utilized, to precisely position and aim the outlet aperture 134 of the passageway-forming catheter at the energy impingement point X on the target tissue T, thereby insuring that, when the tissue penetrating element is advanced out of the outlet aperture 134, it will extend into the target tissue T at a desired site.

Further referring to FIG. 5b, the signal emitting crystal 530 may be alternatively utilized as a signal receiving crystal, such that it will receive reflected ultrasound from the IVUS, as indicated by the dotted arrows on FIG. 5b. Since the signal receiving crystal 530 is specifically positioned and oriented in relation to the outlet 134 and/or path of the tissue penetrating element 150, such receipt of the IVUS ultrasound by the signal receiving crystal 530 will enable the operator to precisely position and rotationally orient the catheter such that the tissue penetrating element 150 will pass directly into the target tissue T, in parallel to the path of reflected ultrasound received by the signal receiving crystal 530.

Figure 5C:
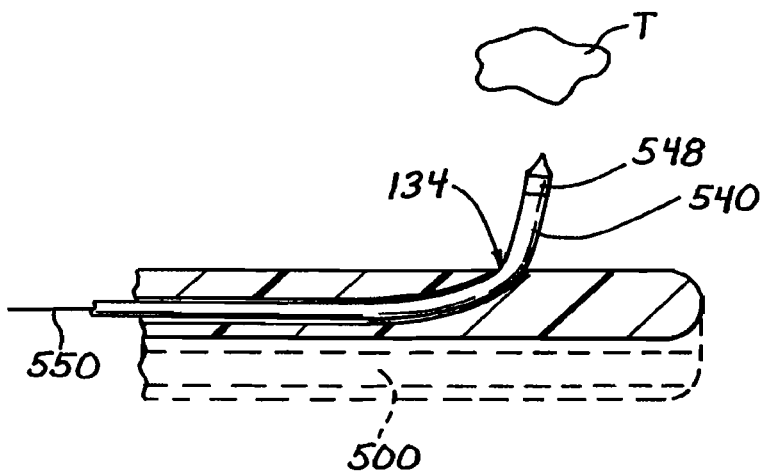
FIG. 5c is a partial longitudinal sectional view of another passageway forming catheter of the present invention having an alternative aiming/positioning system wherein the tissue penetrating element of the catheter is an elongate member having a sensor mounted thereon for sensing the location of the target tissue.

FIG. 5c shows yet another positioning/aiming system wherein the passageway-forming catheter 100d has a working lumen 302 which terminates in a side outlet aperture 134 and through which a tissue-penetrating element 500 in the nature of an elongate member 540 having a sharpened distal end may be advanced through such working lumen 302 and out of the side outlet aperture 134 of the catheter 100d. The elongate member 540 in this embodiment is equipped with a sensor apparatus 548 positioned at or near the sharpened distal end of the elongate member 540. A connector wire 550 may extend longitudinally through the elongate member 540 to permit the sensor 548 to send a signal through the shaft of the member 540 to an extracorporeal location at which such signal may be processed and/or monitored. The sensor 548 may be any suitable type of sensor which will sense the presence and/or location of the intended target tissue T. Parameters or variables which may be sensed by the sensor 548 include temperature, pulse, flow, or other characteristics of the target tissue T, capable of being mechanically, electronically or optically sensed. Additionally or alternatively, an energy emitting or "active" apparatus, such as the energy emitting apparatus 500 described hereabove with reference to FIG. 5, may be positioned within the target tissue T and the sensor 548 formed on the tissue penetrating member 540 may be adapted to receive and sense energy emitted by the active energy emitting member located within the target tissue T. In this manner, the tissue penetrating member 540 serves its own sensing function and enables the operator to control the longitudinal and rotational position of the catheter 100d prior to or during the advancement of the tissue penetrating member 540 out of the outlet aperture 134 and into the target tissue T. It will be appreciated by those skilled in the art, when a tissue penetrating member 540 having an onboard sensor 548 of the type described herein is utilized, such will eliminate the need for any other extracorporeal or intracorporeal imaging or sensing apparatus for aiding in positioning or rotational orientation of the catheter 100b. Alternatively, the catheter 100b may also be provided with other onboard aiming/positioning apparatus or an imaging lumen 300 as described in reference to various other embodiments shown in FIGS. 4-5.

FIG. 5d shows another aiming/positioning system which is similar to that shown in FIG. 5b, but wherein the emitting member 530 (e.g., an ultrasound emitting piezoelectric crystal) is aimed downwardly at the transducer or receiving port of the imaging catheter (e.g., IVUS catheter), and the emitting member 530 is specifically positioned relative to the outlet opening 134 so as to provide an imageable marking at the outlet opening 134. In this manner, the imaging catheter (IVUS catheter) may be used to specifically site and identify the location of the outlet aperture 134, thereby facilitating longitudinal positioning and rotational aiming of the catheter prior to deployment of the tissue penetrating member 150.

FIG. 5e shows one embodiment of a system 790 which may be utilized to facilitate optimization or peaking of the signal received from a sensor or receiving component which is utilized to position and aim the catheter, such as those described hereabove and identified by reference numerals 502, 522, 530 and 548. In this system 790, the wire 510, 521, 531, 550 through which a signal is received from the receiving component 502, 522, 530, 548 is connected to a switch 818. When the switch 818 is open, the signal received will not enter the system 790. However, when the switch 818 is closed, the signal received from the receiving or sensing component 502, 522, 530, 548 will enter a signal conditioning and filtering component 880 wherein the signal will undergo conditioning and filtering. Thereafter this signal will pass through a rectifier 810 wherein the signal will be rectified, and through a leaky integrator 812 of the type well known in the art. Such leaky integrator 812 may comprise a capacitor and a resistor in parallel. The integrated signal from the leaky integrator 812 may then pass into an analog to digital convertor 814, if desired, whereby it will be converted to a digital signal, and such digital signal will then be fed to a display 816 of a type suitable for indicating the relative intensity of the signal received. Such display may be an LED or multiple light display, whereby a column or array of lights are provided and the intensity of the signal received is indicated by the height of the column or the number of lights in the array which are lit at any given time.

In this manner, the system 790 shown in FIG. 5d may be utilized to enable the operator to longitudinally and rotationally move the catheter until the signal received from the receiving component or sensor 502, 522, 530, 548 has been peaked or optimized, thereby indicating that the catheter is properly positioned such that the tissue penetrating element will extend from the outlet 130 into the target anatomical location T.

Figure 6:
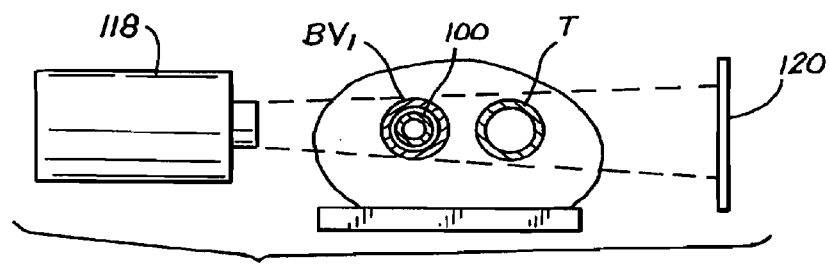
FIG. 6 is a schematic showing of the manner in which an extracorporeal imaging apparatus is useable in conjunction with a marking scheme formed on a passageway-forming catheter of the present invention, to effect precise positioning and rotational orientation of the passageway-forming catheter.
Figure 6A:
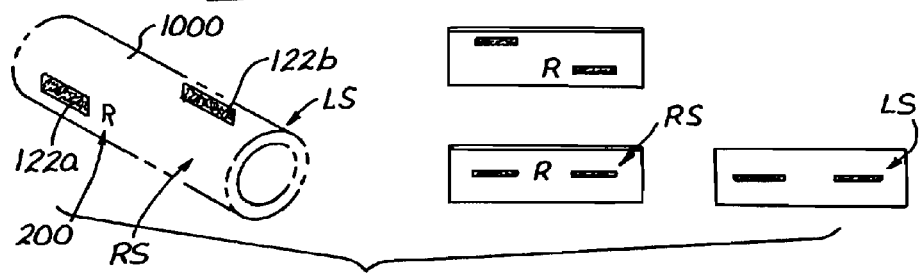
FIG. 6a is a showing of a first marking scheme useable with the extracorporeal imaging system of FIG. 6.
Figure 6B:
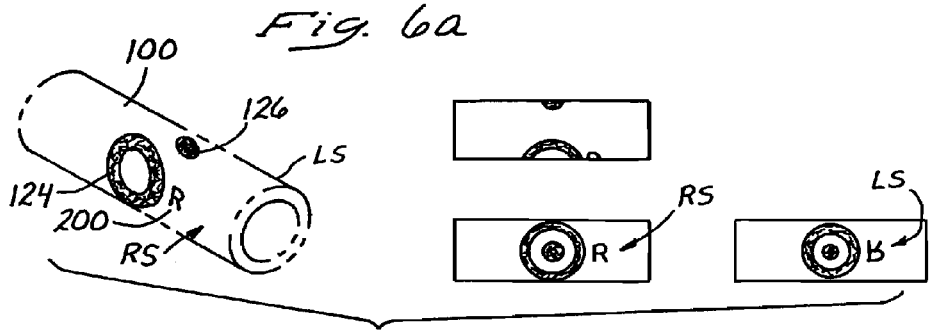
FIG. 6b is a showing of a second marking scheme useable with the extracorporeal imaging system of FIG. 6.
Figure 6C:
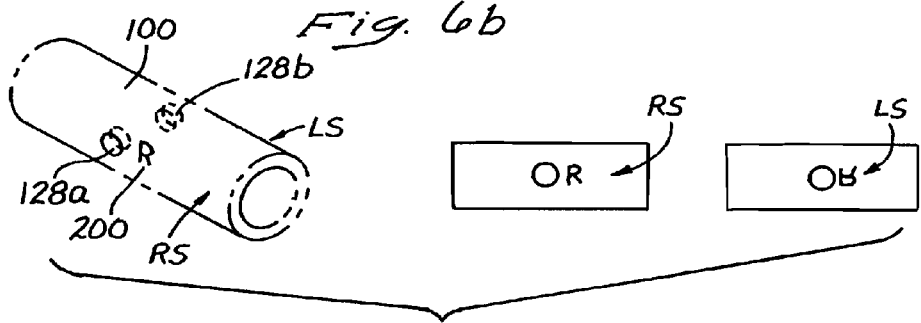
FIG. 6c is a showing of a third marking scheme useable with the extracorporeal imaging system of FIG. 6.

FIGS. 6-6c show other catheter marking schemes which may be used in conjunction with an extracorporeal imaging apparatus 118, such as a fluoroscope, positioned adjacent a mammalian body MB. In the showing of FIG. 6, a catheter 100 has been advanced into the blood vessel BV.sub.1, and such catheter is marked with one of the marking schemes of this embodiment of the present invention. FIGS. 6a-6c show the manner in which the marking scheme of the catheter 100 will appear on the fluoroscopy screen 120 as the catheter is rotated within the blood vessel BV.sub.1.

Referring to FIG. 6a, there is provided a marking scheme which comprises a first radio-opaque linear marking 122 on one side of the catheter body, and a second radioopaque linear marking 122b. The second linear marking 122b is located directly and 180.degree. opposite the first linear marking 122a, but slightly more distal to the first marking 122a. An additional rotation indicating indicia 200, comprising the letter "R" formed of radio-opaque or other imagable material, is formed to the right of the first linear marking 122a. As shown in FIG. 6a, when the catheter is in its desired rotational orientation, the first and second linear markings 122a and 122b will appear next to and in linear alignment with one another on the fluoroscopy screen 120. When such markings 122a and 122b are viewed from the right side RS of the catheter body the rotational marking indicia 200 will appear as the letter "R". However, when the catheter is rotated 180.degree. such that the fluoroscope 118 views the catheter from the left side LS of the catheter body, the rotational marking indicia 200 will appear as the inverted mirror image of the letter "R", thereby informing the operator that the catheter is rotated 180.degree. from the desired rotational orientation.

FIG. 6b shows a similar marking scheme wherein the rotational marking indicia 200 is formed adjacent a radio-opaque circle 24 formed on the right side RS of the catheter body such that, when the catheter body is in its desired rotational position, a radio-opaque dot 126 formed on the left side LS of the catheter body will appear within the circle 124 on the fluoroscopy screen 120, and the rotational marking indicia 200 will appear as the letter "R" to the right of the radio-opaque circle 124. However, when the catheter body is rotated 180.degree. such that the fluoroscope 118 is viewing the left side LS of the catheter body, the rotational marking indicia 200 will appear as the inverted mirror image of the letter "R" on the left side of the circular marking indicia 124, as illustrated in FIG. 6b.

Similarly, as shown in FIG. 6c, the catheter 100 may be provided with two (2) through holes 128a, 128b formed in direct linear alignment with one another on opposite sides of the catheter 100. Adjacent one of the through holes is an imageable marker in the form of the letter "R". When the catheter 100 is rotated such that the through holes 128a, 128b are in direct alignment with the extracorporeal imaging apparatus 118, both through holes 128a, 128b will appear as a single aperture on the image provided on the image viewing apparatus 120. However, when the through holes 128a, 128b are not in direct alignment with one another, they will appear as separate images on the image viewing apparatus 120. In this manner, these through holes 128a, 128b may be utilized to discern the correct rotational orientation of the catheter using an extracorporeal imaging apparatus 118. Similarly, as described hereabove, the letter R will appear differently depending on which side of the catheter 100 is closest to the imaging apparatus 118, thereby avoiding any possible inadvertent 180.degree. mis-rotation of the catheter.

vi. Apparatus for Preventing Inadvertent Deployment of Tissue Penetrating Element FIG. 8 shows another embodiment of the catheter 100e which incorporates apparatus for preventing inadvertent deployment of the tissue-penetrating element 150. In this catheter 100e, a lumen closure member 548 is pivotally mounted on one side of the working lumen 302 through which the tissue penetrating element 150 will pass such that, when in an upwardly pivoted position, such member 548 will block the lumen and prevent inadvertent advancement of the tissue penetrating element out of the opening 134. A balloon 544 or other pressure exerting member is mounted within the body of the catheter 100e, adjacent the blocking member 548 in the embodiment shown, a balloon inflation lumen 546 extends through the catheter to permit alternate inflation and deflation of the balloon. In this manner, when the balloon 544 is inflated, as shown in FIG. 8, the member 548 will pivot upwardly so as to block the working lumen 302 in a manner which will prevent inadvertent deployment of the tissue penetrating element 150. Alternately, when the balloon 544 is deflated, the member 548 will pivot downwardly thereby restoring the working lumen 302 to an open configuration through which the tissue-penetrating element 150 may pass.

FIG. 8' shows another embodiment of the catheter 100e which incorporates apparatus for stabilizing the catheter within a vessel after proper orientation has been confirmed. This apparatus also prevents inadvertent deployment of the tissue penetrating element 150 in combination with the stabilization. In this catheter 100e, a lumen closure member 548' is pivotally mounted near the working lumen 302 through which the tissue penetrating element 150 will pass. The lumen closure member 548' is biased or spring loaded by spring member 998 such that when the balloon, 544' or other pressure exerting member is deflated, lumen 302 is blocked preventing inadvertent advancement of the tissue penetrating element out of the opening 134. A balloon inflation lumen 546 extends through the catheter to permit alternate inflation and deflation of the balloon. After proper orientation of the catheter 100e has been confirmed, the balloon is inflated which causes a portion of the balloon to exit the side of the catheter through exit port 999 which secures the catheter in place within the vessel, 997 as is shown in FIG. 8". Simultaneous with anchoring the catheter in place, inflation of the balloon causes lumen closure member 548' to pivot thereby opening the working lumen 302 to allow advancement of the tissue penetrating element 150.

Materials, construction and treatments of the balloon, 544' may be made to prevent undesired movement or dislodgment in the vessel during its inflated state. Treatment may include surface modification, Dacron, or other means.

It should be appreciated that the general concept of combining an anchoring device which is deployed after confirmation of proper orientation of the tissue penetrating element which simultaneously or nearly thereafter, removes a safety device previously in place to prevent inadvertent advancement of the tissue penetrating element, can be accomplished in other ways not completely described above.

It will be appreciated by those skilled in the art that the invention has been described hereabove with reference to certain presently preferred embodiments and examples only, and no effort has been made to exhaustively describe all possible embodiments and examples in which the invention may take physical form. Furthermore, it will be appreciated that each of the specific components and elements of the above-described embodiments and examples may be combined or used in conjunction with any of the other components shown in relation to other embodiments or examples, to the extent such recombination of elements or components may be accomplished without rendering the device, apparatus, or system unusable for its intended purpose. Furthermore, various additions, deletions, modifications, and alterations may be made to the above-described embodiments and examples without departing from the intended spirit and scope of the invention. Accordingly it is intended that all such variations, recombination, additions, deletions and modifications be included within the scope of the following claims.

What is claimed is:

1. A catheter device, comprising:
    an elongate flexible catheter having a distal portion insertable into a blood vessel of a human subject;
    a tissue penetrating member configured to extend in a first direction from the distal portion of the catheter;
    a balloon exit port in the distal portion of the catheter at a location diametrically opposite a location from which the tissue penetrating member extends;
    a balloon which, when inflated, protrudes out of the balloon exit port in a second direction opposite the first direction; and
    a lumen extending through the catheter and useable for inflation and deflation of the balloon.

2. The catheter device of claim 1 wherein the tissue penetrating member comprises a hollow needle.

3. The catheter device of claim 1 wherein the tissue penetrating member is configured to penetrate a wall of the blood vessel when the balloon is at least partially inflated.

4. The catheter device of claim 1, further comprising rotational marking indicia at the distal portion of the catheter, wherein the rotational marking indicia are useable for rotational adjustment of the distal portion of the catheter within the blood vessel to aim the tissue penetrating member toward an intended target location prior to inflation of the balloon.

5. The catheter device of claim 4 wherein the rotational marking indicia comprise radiographic markings.

6. The catheter device of claim 5 wherein the radiographic markings are imageable by an extracorporeally positioned imaging apparatus.

7. The catheter device of claim 1 wherein the catheter extends along a catheter axis, and wherein the first direction is lateral to the catheter axis.

8. The catheter device of claim 1 wherein the tissue penetrating member comprises an advanceable member.

* * * * *

UNITED STATES PATENT AND TRADEMARK OFFICE
CERTIFICATE OF CORRECTION

PATENT NO. : 9,713,483 B2  
APPLICATION NO. : 14/199901  
DATED : July 25, 2017  
INVENTOR(S) : Makower et al.

Page 1 of 1

It is certified that error appears in the above-identified patent and that said Letters Patent is hereby corrected as shown below:

On the Title Page

Item (72) Inventor is corrected to read:
-- Joshua Makower, Los Altos, CA;
J. Christopher Flaherty, Los Altos, CA;
Timothy R. Machold, Moss Beach, CA;
Jason B. Whitt, San Francisco, CA;
Philip Christopher Evard, Palo Alto, CA;
Patrick Edward Macaulay, San Jose, CA;
John Thomas Garibotto, Newark, CA;
Margaret W. Tumas, Orinda, CA;
Alan Robert Selfridge, Los Gatos, CA --.

Signed and Sealed this
Fourteenth Day of August, 2018

Andrei Iancu
*Director of the United States Patent and Trademark Office*